United States Patent
Rousseau et al.

(10) Patent No.: US 10,588,769 B2
(45) Date of Patent: Mar. 17, 2020

(54) CALORIC BYPASS DEVICE

(71) Applicant: Ethicon, Inc., Somerville, NJ (US)

(72) Inventors: Robert Anthony Rousseau, Ottsville, PA (US); Kevin Shaun Weadock, Hillsborough, NJ (US)

(73) Assignee: Ethicon, Inc., Somerville, NJ (US)

(*) Notice: Subject to any disclaimer, the term of this patent is extended or adjusted under 35 U.S.C. 154(b) by 375 days.

(21) Appl. No.: 15/291,286

(22) Filed: Oct. 12, 2016

(65) Prior Publication Data
US 2018/0098870 A1  Apr. 12, 2018

(51) Int. Cl.
*A61F 5/00* (2006.01)
*A61F 2/04* (2013.01)

(52) U.S. Cl.
CPC .............. *A61F 5/0076* (2013.01); *A61F 2/04* (2013.01); *A61F 5/0036* (2013.01); *A61F 2002/045* (2013.01)

(58) Field of Classification Search
CPC .... A61F 2002/045; A61F 2/04; A61F 5/0076; A61F 5/0036
See application file for complete search history.

(56) References Cited

U.S. PATENT DOCUMENTS

| | | | |
|---|---|---|---|
| 4,134,405 A | 1/1979 | Smit | |
| 4,315,509 A * | 2/1982 | Smit | A61F 5/0076 417/474 |
| 4,501,264 A | 2/1985 | Rockey | |
| 4,641,653 A | 2/1987 | Rockey | |
| 4,763,653 A | 8/1988 | Rockey | |
| 5,306,300 A | 4/1994 | Berry | |
| 5,820,584 A | 10/1998 | Crabb | |
| 7,794,447 B2 | 9/2010 | Dann et al. | |
| 9,149,383 B2 * | 10/2015 | Schwab | A61F 5/003 |
| 2003/0040804 A1 | 2/2003 | Stack et al. | |
| 2003/0040808 A1 | 2/2003 | Stack et al. | |
| 2003/0093117 A1 | 5/2003 | Saadat | |
| 2003/0120265 A1 | 6/2003 | Deem et al. | |
| 2003/0144708 A1 | 7/2003 | Starkebaum | |
| 2007/0282454 A1 | 12/2007 | Krueger | |
| 2010/0016988 A1 * | 1/2010 | Stack | A61F 2/04 623/23.65 |
| 2012/0041393 A1 | 2/2012 | Ahmann | |

(Continued)

OTHER PUBLICATIONS

Trout, D.L. et al. "Dietary Influences on Gastric Emptying of Carbohydrate versus Fat in the Rat", Journal of Nutrition, 1977, vol. 107, pp. 104-111.

(Continued)

*Primary Examiner* — Leslie R Deak

(57) ABSTRACT

A novel caloric bypass device that is inserted through the oral cavity and into the digestive tract of a human is disclosed. The device is deliverable as either a unitary or modular structure that preferentially directs a significant volume of the high calorie fluidic components of the chyme through the digestive tract, preventing exposure to the absorptive tissues of the digestive tract and, in some forms, stimulates negative feedback to the patient when simple sugars and carbohydrates are consumed. Also disclosed is a novel method of reducing or restricting caloric intake using this device to prevent or minimize contact with the absorptive tissues of the digestive tract.

8 Claims, 21 Drawing Sheets

(56) References Cited

U.S. PATENT DOCUMENTS

| | | |
|---|---|---|
| 2014/0275747 A1 | 9/2014 | Connor |
| 2014/0343477 A1 | 11/2014 | Sharvit |
| 2016/0106565 A1 | 4/2016 | Sharvit |
| 2018/0116850 A1* | 5/2018 | Pattison ................ A61F 5/0033 |

OTHER PUBLICATIONS

International Search Report dated Dec. 21, 2017 for Appln. No. PCT/US2017/054885.

* cited by examiner

CALORIC BYPASS DEVICE

FIELD OF THE INVENTION

The field to which this invention pertains is medical devices, more particularly medical devices useful in caloric intake restriction.

BACKGROUND OF THE INVENTION

According to studies reported by the Centers for Disease Control and Prevention (CDC), the National Health and Nutrition Examination Survey (NHANES) and the National Health Interview Survey (NHIS), more than two-thirds (68.8 percent) of adults over 20 years of age are considered to be overweight or obese. Additionally, more than one-third (35.7 percent) of adults are considered to be obese and more than 1 in 20 (6.3 percent) have extreme obesity.

Additionally, the National Institute of Health reports that overweight and obesity are risk factors for type 2 diabetes, heart disease, high blood pressure, and other health problems such as nonalcoholic fatty liver disease (excess fat and inflammation in the liver of people who drink little or no alcohol), osteoarthritis (a health problem causing pain, swelling, and stiffness in one or more joints), some types of cancer including breast, colon, endometrial (related to the uterine lining), and kidney, as well as stroke.

Not exclusively a United States problem, worldwide obesity ranges are also increasing dramatically. The World Health organization reports that Worldwide obesity has more than doubled since 1980 and in 2014, more than 1.9 billion adults, 1.8 years and older, were overweight. Of these over 600 were obese.

There is no single cause of overweight and obesity, and, although the physiology and psychology of obesity are complex, the medical consensus is that the key contributing factor is an over intake of calories combined with reduced energy expenditures. There is no single approach that can help prevent or treat overweight and obesity. Conventional treatments may include a mix of behavioral therapy, diet, exercise, and sometimes weight-loss drugs. In some cases of extreme obesity, weight-loss surgery may be a preferred option.

Bariatrics is the field of medicine encompassing the study of overweight and obesity, its causes, prevention and treatment. Bariatric surgery is a treatment for morbid obesity that involves the surgical alteration of a patient's digestive tract to encourage weight loss and to help maintain normal weight. Known, conventional bariatric surgical procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty.

There have been many attempts in the past to surgically modify patients' anatomies to attack the over consumption problem by reducing the desire to eat. Stomach stapling, or gastroplasties, to reduce the volumetric size of the stomach, therein achieving faster satiety, were performed in the 1980's and early 1990's. Although patients undergoing such procedures were able to achieve early weight loss, sustained reduction was not typically obtained. The reasons for these outcomes are not all known, but are believed related to several factors. One of which is that the stomach stretches over time increasing its volume while psychological drivers motivate patients to find creative approaches to literally eat around the smaller pouch.

There are two conventional surgical procedures that have been observed to successfully produce long-term weight loss; the Roux-en-Y gastric bypass and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the Duodenum makes it more difficult to digest fats, high sugar and carbohydrate rich foods. One objective of the surgery is to provide feedback to the patient by producing a dumping syndrome if the patient does eat these food products. Dumping occurs when carbohydrates directly enter the jejunum without being first conditioned in the Duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes.

Although the physiology seems simple, the exact mechanism of action in these procedures is not understood. Negative feedback is provided from both regurgitation into the esophagus and dumping when large volumes of the wrong foods are eaten. Eventually, patients learn that in order to avoid both of these issues they must be compliant with the dietary restrictions imposed by and resulting from their modified anatomy. In the BPD procedure, large lengths of jejunum are bypassed resulting in malabsorption and therefore, reduced caloric uptake. In fact, the stomach is not reduced in size as much in the BPD procedure so that the patient is able to consume sufficient quantities of food to effectively compensate for the reduced absorption. This procedure is reserved for the most morbidly obese as there are several known serious side effects of prolonged malabsorption.

Laparoscopic techniques have been applied to these surgeries in an attempt to improve the patient outcomes. While the laparoscopic techniques provide fewer surgical complications, e.g., hospital acquired infections, etc. they continue to expose these very ill patients to high operative risk in addition to requiring an enormous level of skill by the surgeon.

While surgery seems to be an effective answer in the treatment of overweight and obesity, the current invasive procedures present risks that are frequently not acceptable in view of the observed complication rates. Additionally, the medical devices that have been proposed for use in the treatment of overweight and obesity in the literature, as well as the surgical approaches, provide a general approach of malabsorption of all nutritional components of the ingested foods. Further, the most favorable surgical procedure functions by the elimination of contact of ingested food with the absorptive tissues of the Duodenum. The mechanism of the bypass, while not being fully understood, appears to limit the absorption of the carbohydrate and simple sugar components of the ingested food, as evidenced by the generally immediate reduction in the blood sugar levels of treated patients. Additionally, medical devices or newer surgical approaches that demonstrate this reduction of blood sugars are deemed successful, despite the potential creation of generalized malnutrition.

In the article "Dietary Influences on Gastric Emptying of Carbohydrate versus Fat in the Rat", by Trout et. al., published in the Journal of Nutrition; 107: 104-111, 1977, it was determined that "gravity tends to hold back the fat from leaving the stomach, allowing glucose in aqueous solution to be preferentially emptied" and further that "a sizable portion of the starch in starch-containing meals became suspended in water during and shortly after being ingested, and the starch suspension was then emptied from the stomach preferentially to fat-containing particulate matter". It would appear that this functionality of the natural separation of the glucose, or solubilized sugars, as well as the suspended starches and the subsequent acceleration of these components through the pyloric valve into the Duodenum could be eliminated and thereby prevent the blood sugar from elevating while not inhibiting the absorption of the necessary dietary nutrients that are critical to cellular survival.

In U.S. Pat. Nos. 4,501,264; 4,641,653 and 4,763,653, Rockey discloses medical sleeve devices for placement in a patient's stomach. The medical sleeve described in these patents is intended to reduce the surface area available for absorption in the stomach without affecting the volume of the stomach, nor will the device described isolate ingested food from stomach secretions. The medical sleeve is not configured to be deployed in a patient's small intestine and will not have an appreciable impact on the digestion of the ingested food.

In U.S. Pat. No. 4,134,405 (Smit), U.S. Pat. No. 4,315,509 (Smit), U.S. Pat. No. 5,306,300 (Berry), and U.S. Pat. No. 5,820,584 (Crabb), sleeve devices are described that are intended to be placed at the lower end of the stomach and therefore do not serve to isolate ingested food from the digestive secretions of the stomach. These sleeve devices are not configured to be deployed in a patient's stomach or to effectively reduce the volume of the patient's stomach or small intestine.

In U.S. Patent Application US 2003/0040804, Stack et al. describe a satiation device to aid in weight loss by controlling feelings of hunger. The patent application describes an antral tube that expands into the Antrum of the stomach to create a feeling of satiation. The devices described are not configured to isolate ingested food and liquids from digestive secretions in the stomach or the intestines.

In U.S. Patent Application US 2003/0040808, Stack et al. describe a satiation device for inducing weight loss in a patient that includes a tubular prosthesis positionable at the gastro-esophageal junction region, preferably below the z-line. The prosthesis is placed such that an opening at its proximal end receives masticated food from the esophagus, and such that the masticated food passes through the pouch and into the stomach via an opening in its distal end. The pouch serves to delay the emptying of food into the stomach, thereby providing the patient a sense of fullness prior to filling the stomach.

In U.S. Patent Application US 2003/0093117, Sadaat describes an implantable artificial partition that includes a plurality of anchors adapted for intraluminal penetration into a wall of the gastro-intestinal lumen to prevent migration or dislodgement of the apparatus, and a partition, which may include a drawstring or a toroidal balloon, coupled to the plurality of anchors to provide a local reduction in the cross-sectional area of the gastro-intestinal lumen. The reduction in the cross sectional area of the lumen delays motility of ingested food, thereby increasing the sense of satiety that the patient experiences.

In U.S. Patent Application US 2003/0120265, Deem et al. describe various obesity treatment tools and methods for reducing the size of the stomach pouch to limit the caloric intake as well as to provide an earlier feeling of satiety. The smaller pouches may be made using individual anchoring devices, rotating probes, or volume reduction devices applied directly from the interior of the stomach. A pyloroplasty procedure to render the pyloric sphincter incompetent and a gastric bypass procedure using atraumatic magnetic anastomosis devices are also described.

In U.S. Patent Application US 2003/0144708, Starkebaum describes methods and systems for treating patients suffering from eating disorders and obesity using electrical stimulation directly or indirectly to the Pylorus of a patient to substantially close the Pylorus lumen to inhibit emptying of the stomach In US Patent Application 2014/0275747, Connor discloses a device that is comprised of two passages for food to travel through a patient's digestive tract, referred to as an adjustable gastrointestinal bifurcation. The device has two openings that are regulated by a flow control member that may at least partially direct ingested food into either opening. The bifurcated device is comprised of two openings that are located at the superior end of the device just below the esophageal sphincter. The flow control member is capable of adjustment from a remote location and may direct food into either a passage that enables absorption of nutrients or a second passage that limits the absorption of nutrients. While the device can divert various food types, it requires a conscious effort on behalf of the user or physician to set the diversion pathway into the correct location for the specific food type that has been ingested. An alternative form of the device requires the implantation and use of a remote sensor within the upper GI tract to sense the type of food being ingested to direct the flow control member. This would require the presence of an invasive foreign object within the upper GI tract, particularly the oral cavity, which would likely be intolerable to the patient.

In U.S. Pat. No. 7,794,447, Mitchell et. al. describe bypass type tubular devices that may be produced with valves and restrictors to control the exposure of ingested food to digestive secretions. The devices as disclosed form a passage between the upper portion of the stomach, or lower portion of the esophagus, through which ingested food particles will pass. The passage may be produced with valves or increased porosity, enabling digestive secretions to enter the passage to digest the food contained therein and also enabling reverse passage of partially digested nutrients to flow back into contact with the absorptive tissues of the GI tract. The restrictive passage may extend as far as the ileum to allow the discharge of partially digested material into portions of the GI tract that may respond and cause the body to eliminate the undigested food from the GI tract. The device, as disclosed, does not differentiate between healthy and unhealthy ingested materials and primarily functions to limit the digestive processes. In the most restrictive form of the device, difficult to digest materials, such as complex proteins, would pass undigested into the ileum and therefore be eliminated from the body without imparting any benefit to the patient.

There remain unmet needs in this art to provide medical devices that are capable of re-directing the most damaging components of ingested food, that are reversible, that do not inhibit the digestion of healthy components of ingested food, that do not rely on patient inputs to function properly, and that provide negative biological feedback to inhibit the ingestion of simple sugars and carbohydrates.

There also remains a need in this art for less invasive methods of altering patients eating behavior while reducing the dietary impact of foods that are incompatible with diabetic metabolic disorders and novel medical devices for facilitating such methods.

SUMMARY OF THE INVENTION

Therefore, a novel caloric bypass device for implantation into the gastrointestinal tract is disclosed. The device has a continuous, compliant wall defining an inner cavity. The wall has an inner surface and an outer surface, and the wall is permeable in part to fluids and entrained particles. The wall has a configuration. The device has a tubular member having a lumen extending from the wall, said lumen in fluid communication with the cavity. The device has a top and a bottom.

Another aspect of the present invention is a novel caloric bypass device. The device has an outer tubular member having a top, a bottom, a central section, an outer surface and an inner surface. The device has an inner tubular member having a top, a bottom, an outer surface, and an inner surface and a lumen. The inner tubular member defines an inner lumen. The inner tubular member is mounted in the lumen of the outer tubular member such that the top of the inner tubular member is engaged with the top of the outer tubular member to form a fluid-tight seal, and the bottom of the inner tubular member is engaged with the bottom of the outer tubular member to form a fluid-tight seal. There is a channel between the inner surface of the outer tubular member and the outer surface of the inner tubular member and an elastic member contained with the channel. There is at least one fluid permeable section in the inner tubular member. A tubular extension member is mounted to the device in fluid connection with the channel. There is optionally a valve in communication with the inner lumen adjacent to the bottoms of the outer tubular member and the inner tubular member. The device has a top and a bottom.

Yet another aspect of the present invention is a novel caloric bypass device. The device has a hollow structure having a top and a bottom; the structure has an inner volume defined by a compliant wall. The compliant wall has an inner surface, and an outer surface, wherein at least part of the wall is fluid permeable. There is an elastic element contained within the volume. There is an upper portion mounted to the top of the hollow structure, the upper portion having a section for engaging the lower esophageal sphincter and receiving ingested materials. A macroporous element is associated with the upper portion for separating fluid from solids in the ingested materials. A valve associated with the upper portion provides for the release of separated solids into the stomach. There is also a fluid channel in communication with the macroporous element; and, a tubular member in fluid communication with the fluid channel and the inner volume.

Further aspects of the present invention are methods of restricting caloric intake using the above-described caloric bypass devices.

These and other aspects and advantages of the present invention will become more apparent from the following description and accompanying drawings.

DETAILED DESCRIPTION OF THE INVENTION

Figure 1:
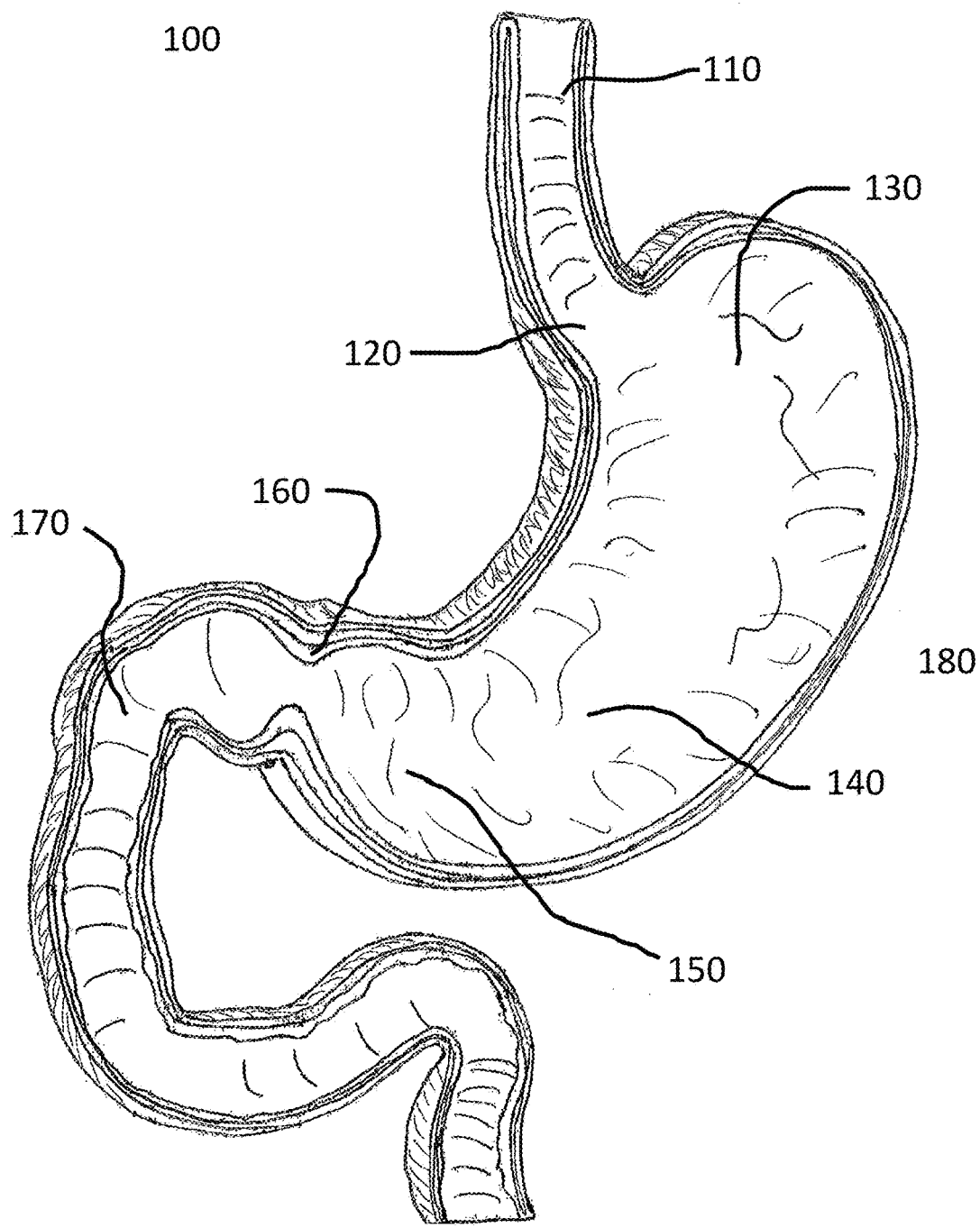
FIG. 1 is a cross-sectional view of the upper middle portion of the human gastrointestinal tract.

Referring to FIG. 1, the upper middle portion of the human gastrointestinal tract 100 is diagrammatically illustrated. The esophagus 110 leads to the lower esophageal sphincter 120. The lower esophageal sphincter 120 is located at the entry point into the stomach 180 and serves to admit ingested particles of food into the stomach and to subsequently form a seal, when constricted, to prevent the regurgitation of food particles and digestive fluids into the esophagus 110 during the muscular contractions associated with the digestive process. The food enters the stomach 180 through lower esophageal sphincter 120 near the Fundus 130 and is subjected to the digestive secretions of the stomach lining. As the digestive contractions of the Fundus 130 occur, the food passes towards the Antrum 140 and ultimately passes into the Pylorus 150 of the stomach 180 where it is subjected to strong contractions and the liquefied portion of the semi-digested material, or chyme, is passed into the Duodenum 170 through the dilation of the Pyloric valve 160.

Figure 2:
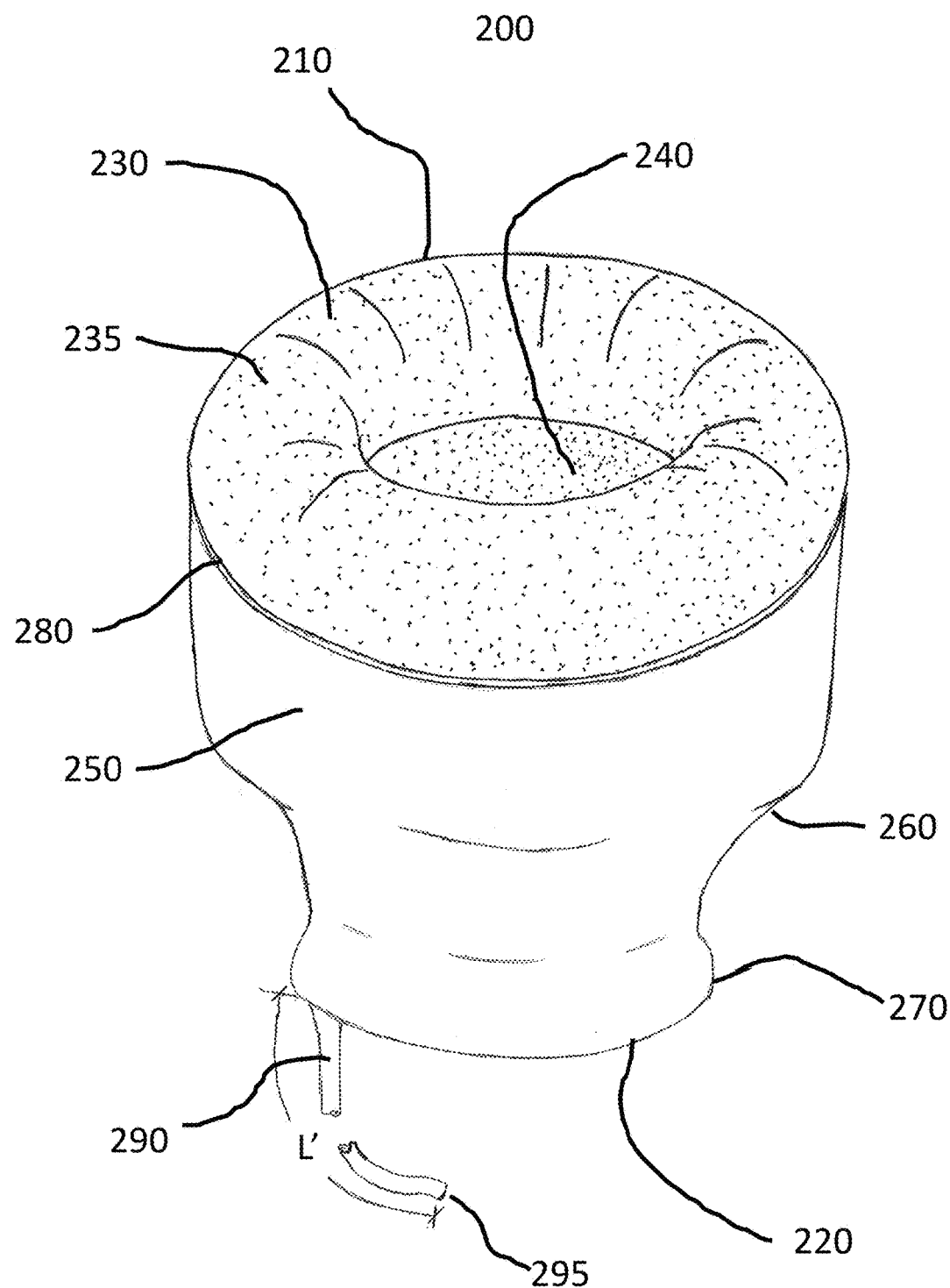
FIG. 2 is a perspective view of an embodiment of a double walled caloric bypass device of the present invention.
Figure 3:
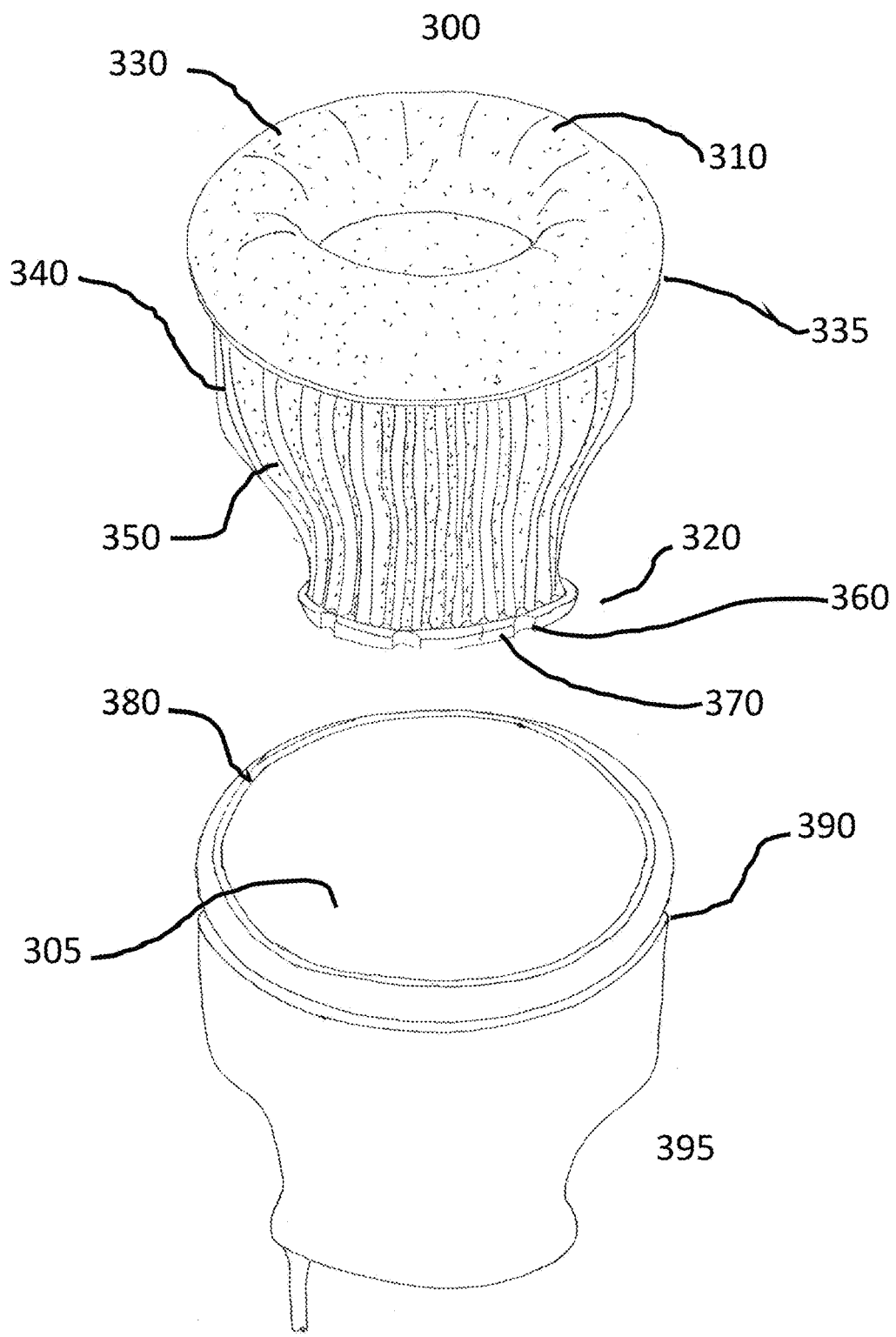
FIG. 3 is an exploded perspective view of the bypass device of FIG. 2.
Figure 4:
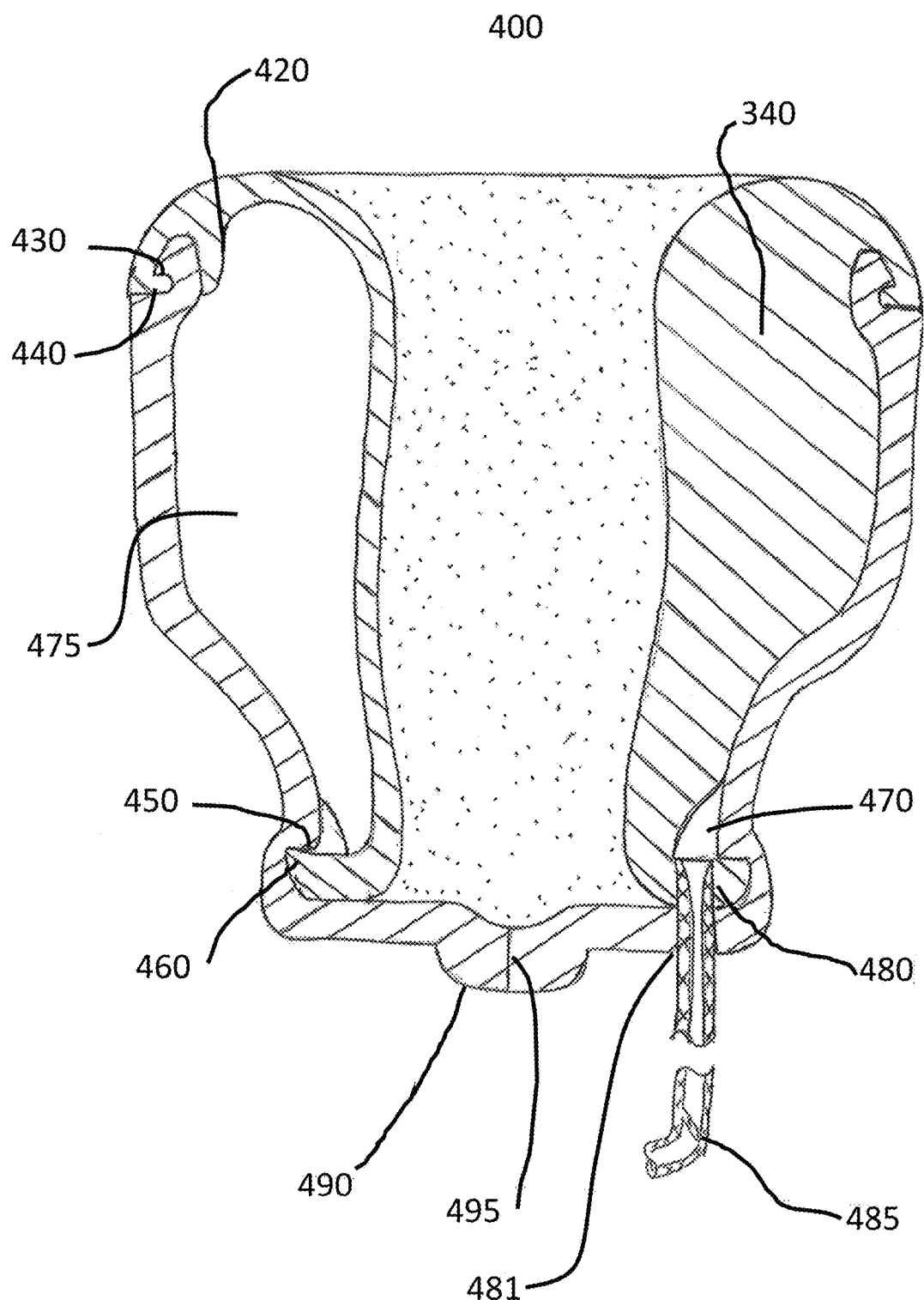
FIG. 4 is a cross-sectional view of the bypass device of FIG. 2.
Figure 7:
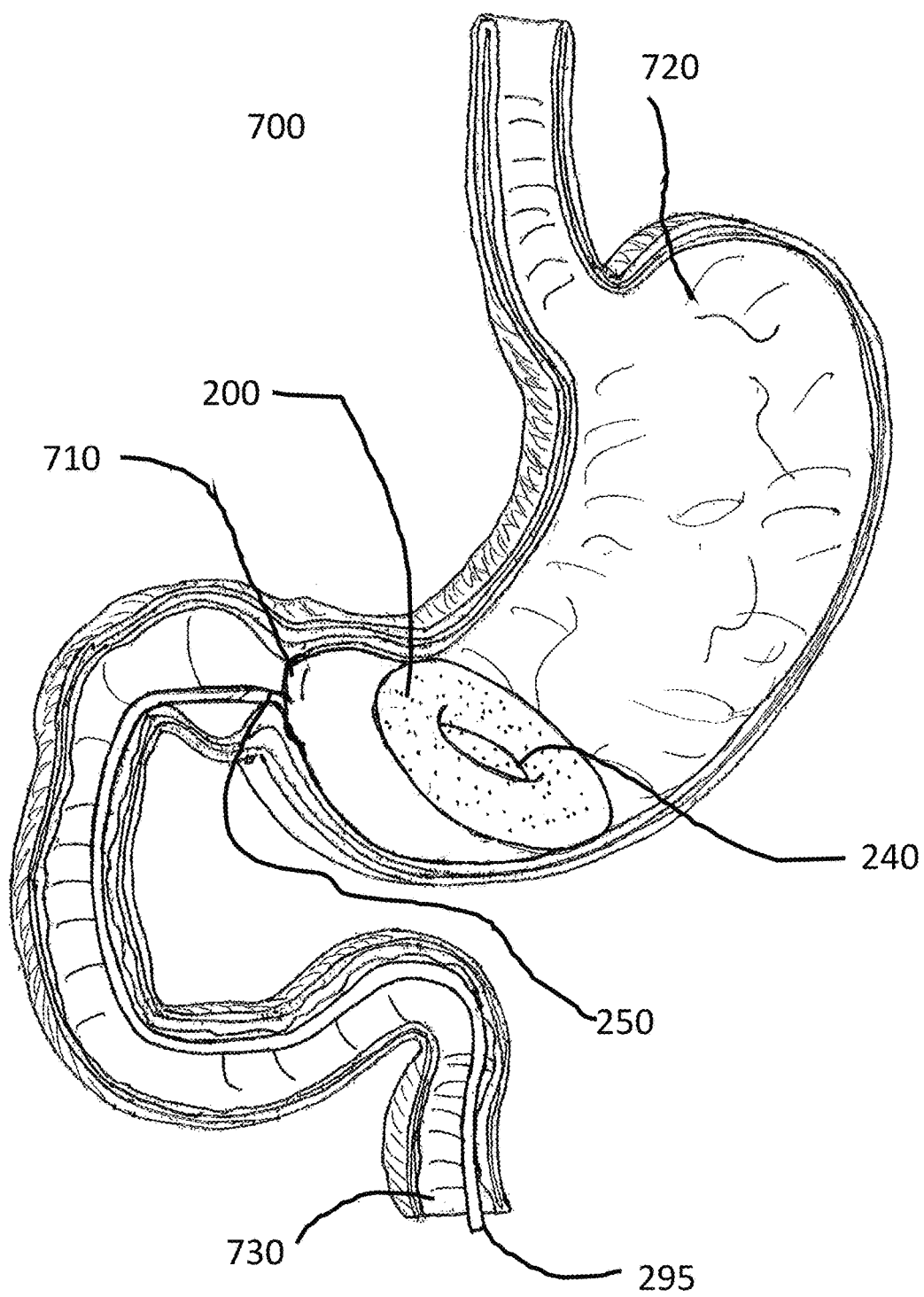
FIG. 7 shows the upper middle portion of the human gastrointestinal tract of FIG. 1 with the bypass device of FIG. 2 deployed within the Antrum.

Referring to FIG. 2, an embodiment of the double-walled caloric bypass device 200 is illustrated. The device is somewhat conical in overall shape or configuration with a truncated end, although sections of the device can be described as cylindrical. Device 200 is seen to have an upper surface 210 and a lower end 220, and an inner lumen 240. There is an outer tissue contacting surface 250 that, when the device is deployed, is in contact with portions of the lining of the stomach 180 as seen in FIG. 7. In this particular embodiment, the bypass device 200 has been designed to engage with the tissue of the transitional region of the Antrum 140 and the Pylorus 150 with the main body of the device 200 intended to fit within the Pylorus 150. In order to accommodate the transitional region, the device 200 has a slightly contoured surface geometry 260 extending from the central region to the lower end 220. Additionally, there is an expanded diameter, flange-like region 270 located at the lower end 220 of the device. The extension tube 290 is produced with a length that is deemed acceptable to the anatomy of the typical bariatric patient. The length L' provides adequate tubing to enable the exit to reach the ileum of the intended patient. The extension tube 290, as illustrated, is produced as thin walled collapsible tubular element; however, it may also include at least a portion of a corrugated structure to resist fully collapsing in critical regions. The tubular element may also be produced from welded web materials with a small diameter cord-like element that extends along the entire length of the tube element to the exit 295. The thin cord-like element maintains the flat web style tube lumen in an open condition and prevents the web style tube from kinking or fully collapsing. Any of these styles of tubing may be included in the structure to achieve benefits specifically tailored to the various portions of the GI tract. The upper surface 210 of the device 200 as well as the inner lumen 240 is produced from a material that is porous 235 or has a series of valves contained within it. The valves may be of rudimentary design whereby they are produced through the puncturing of the material with a stylus to produce an angular cut. This style of cutting produces a flap style valve that is able to be pressed inward, away from the lumen of the device, to provide access to the contained space within the double walled device 200. The valve elements seal against the cut surface when the forces are reversed. The union 280 of the inner and outer walls of the device extends about the perimeter of the outer and inner wall components and is hermetically sealed. It may be desirable to produce the device as a modular unit in which case the seal may be produced through a mechanical interference of the mating components Referring to FIG. 3, an exploded perspective view illustration 300 of the embodiment of FIG. 2 is provided. The upper flange portion 310 of the inner wall component 330 is semi-toroidal shaped. The flange has a rim 335 that abuts with the mating receiver 395. The receiver 395 has an inner lumen 305 and interlocking rim geometry 380. The interlocking rim geometry 380 is shaped as a generally conical shape and abuts an undercut feature 390 intended to receive the mating feature on the inner wall component 330. The external lower wall 350 of the inner wall component is produced with a series of standing rib-like elements 340 that are flexible in nature. Additionally, the lower inner wall component end 320 of the inner wall component 330 is provided with a rim-like interlocking feature 370. Within this rim feature 370, there may be optional scalloped locations 360 where the rim 370 is discontinuous. The discontinuous rim 370 may facilitate assembly of the inner wall component and the outer receiver component Referring to FIG. 4, a cross-sectional view 400 of the assembled caloric bypass device 200 is illustrated. The inner wall component 330 is produced with interlocking receiver features on both ends of the device. The upper end is produced with an abutting undercut feature 440 about the inner perimeter of the rim feature. The abutting undercut feature 440 of the inner wall component 330 mates with a c-shaped undercut feature 430 on the rim of the receiver component. Additionally, an optional engagement feature in the form a wall extension 420 is illustrated to facilitate a tighter fit of the interlocking components and to ensure a hermetic seal is achieved. The opposing end of the two interlocked components has interlocking mating features in the form of a pocketed undercut 450 in the inner lumen of the receiver component 395 and a flange like feature 460 on the inner wall component 330. The cross-sectional view of one of the standing rib-like elements 340 is illustrated. The standing rib-like element 340 is a thin walled element which is subject to buckling when lateral compressive loading is applied. There is at least one standing rib-like element provided about the perimeter of the inner wall component 330. Preferably, there is a plurality of standing rib-like elements 340 provided about the perimeter of the inner wall component. The standing rib-like elements are spaced apart to form vertical channels 475 in between each pair of adjacent standing rib-like elements. It should be noted that the standing rib-like elements 340 do not extend along the full length of the inner wall component 330. As such, there is a continuous channel 470 formed about the perimeter of the lower inner wall component end 320 of the inner wall component that is in fluid communication the vertical channels previously described. When the inner wall component 330 is assembled into the receiver component 395, the clearance of the inner wall component 330 and mating receiver component 395 enables all of the vertical channels 475 between the standing rib-like elements to be in fluid communication about the perimeter of the base of the assembled caloric bypass device 200. The continuous channel 470 is in fluid communication with the extension tube proximal lumen 480 of the extension tube 290. The anti-reflux valve 485 is included within the extension tube 290; however, an anti-reflux valve may be included directly in the exit port 481 of the assembled device. The lower end of the device 220 is formed with an integral flow restrictor 490 formed as part of the mating receiver 395. The flow restrictor 490 is a simple slit 495 or cut style valve in the elastic material. Alternatively, non-integral conventional valves may be utilized or simple constricted geometries that may impede the flow of the chyme may also be utilized. The inclusion of the flow restrictor 490 at the lower end 220 of the caloric bypass device 200 essentially forms a pocketed shape to the inner portion of the device.

Figure 5:
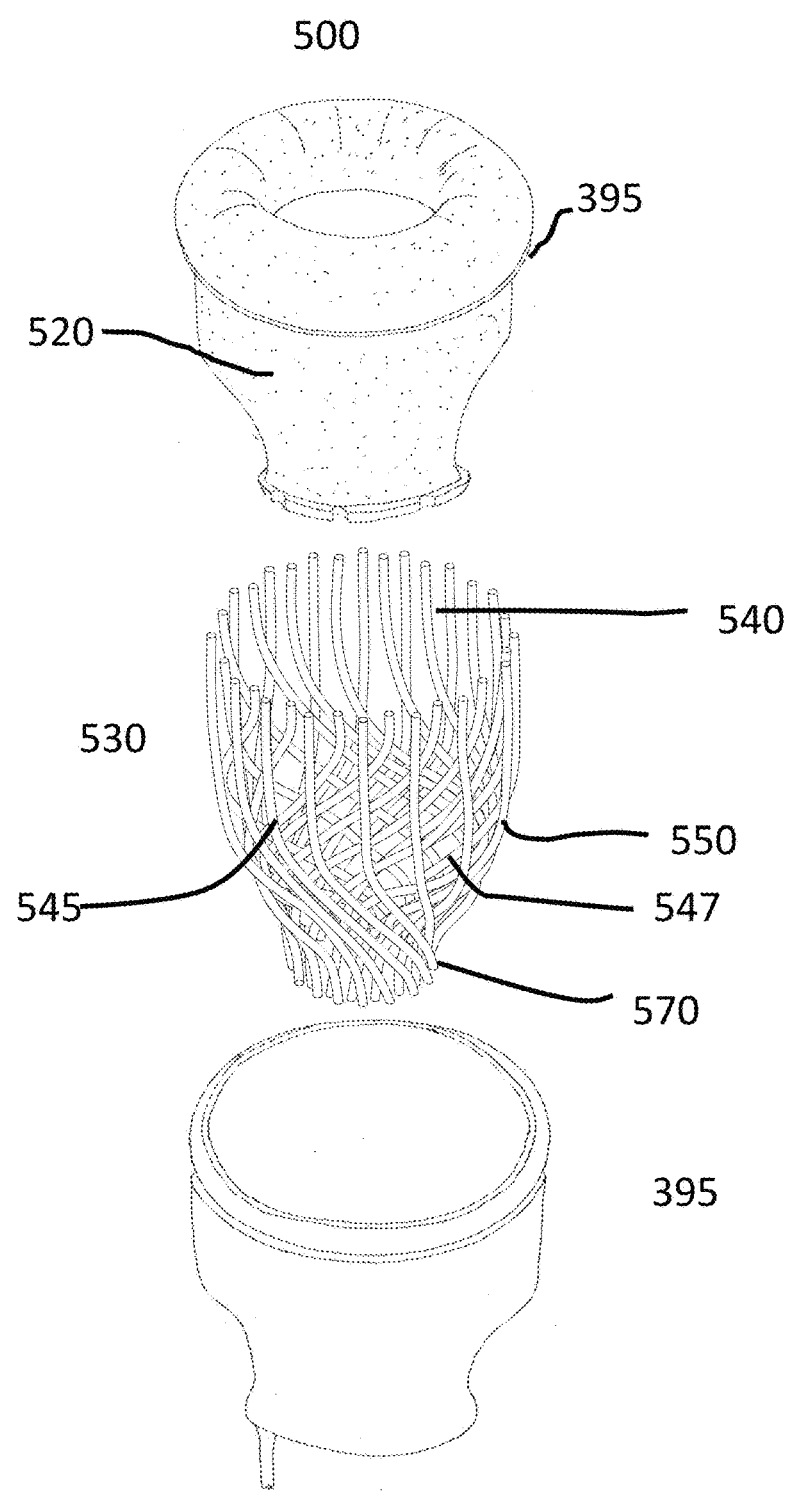
FIG. 5 is an exploded perspective view of an alternate embodiment of a bypass device of the present invention; the device has an intermediary support structure.

Referring to FIG. 5, an exploded perspective view of an alternate form of the extraction device 500 is illustrated. In this embodiment, the inner wall component 330 is produced with a smooth wall 520 free of the standing rib-like elements 340 previously described. The mating receiver 395 is identical to the previously described device. The elastic separator function of the standing rib-like elements 340 is provided through the use of an intermediary support structure 530. The intermediary support structure 530 is produced through the use of counter wound fiber like elements 550. In order to wind the fiber like elements 550, a mandrel that is formed into a shape that is similar to, and sized comparable to the exterior profile of the inner wall component 330. The inner fibers 540 are spaced apart and are wound in a clockwise direction in a spiral pattern that converges at the intermediary element distal end 570. The layer of outer fibers 545 are wound in a counter-clockwise direction, in converging pattern at the intermediary element distal end 570 thereby producing a mesh like structure. The counter wound fiber elements are subjected to a bonding process that may be chemically, or thermally based to create a fusion of the intersecting points of the fibers. In this fused configuration, the counter wound fiber structure provides an elastic separator function when placed between in the inner wall component 330 and the mating receiver 395. Additionally, the fiber spacing, coupled with the counter wound and layered orientation, produce a series of irregular channels 547 that are in fluid communication about the entire surface of the interlocked fiber like elements 550.

Figure 6:
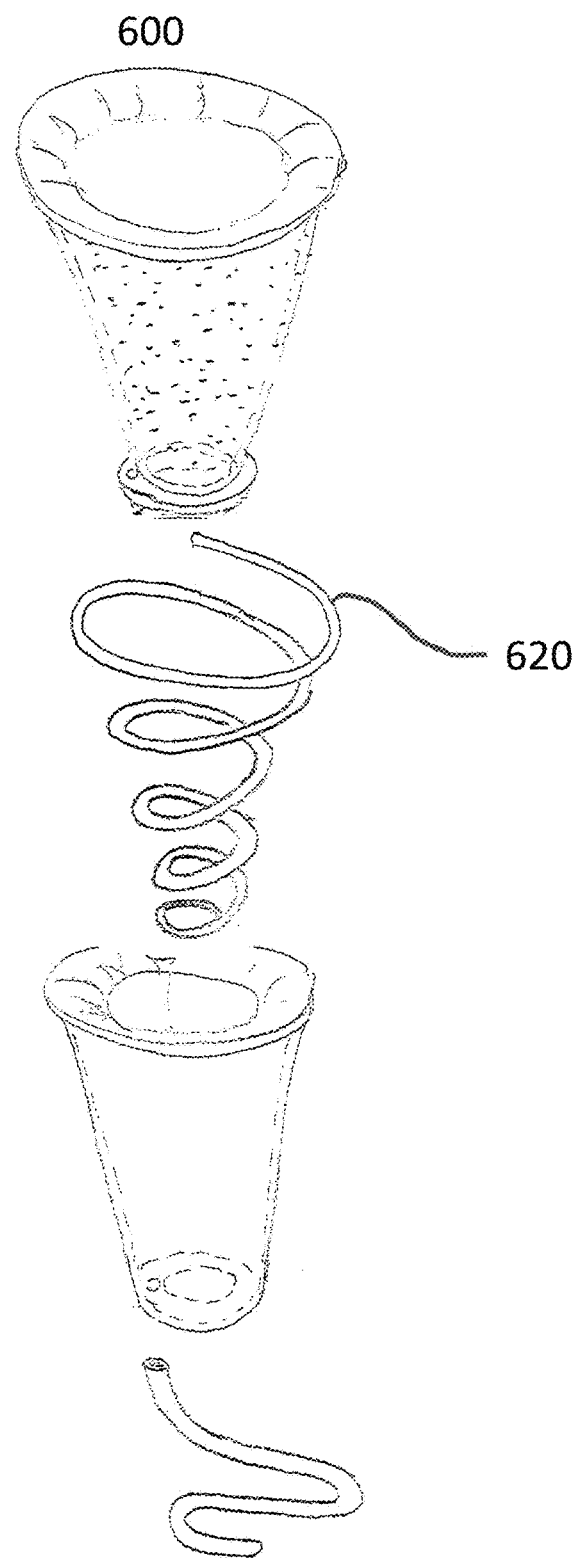
FIG. 6 is an exploded perspective view of another alternate embodiment of a bypass device of the present invention.

Referring to FIG. 6, an exploded perspective illustration of an alternate embodiment 600 is disclosed. It can be seen that the device 600 is somewhat similar to those previously described; however, the device 600 is more conically shaped without contours. Also, the elastic separator function is provided through the use of a spiral shaped elastic element 620. The inner wall component 330 and the mating receiver 395 are interlocked and bonded together along the opposing ends as previously described.

Referring to FIG. 7, a human stomach with the caloric bypass device 200 deployed within the Antrum 140 is illustrated 700. While the caloric bypass device 200 may be designed to be deployed at any location within the stomach, the embodiment as described is placed within the Antrum 140 near the upper portion of the Pylorus 150.

Ingested food particles enter the stomach as they are passed through the lower esophageal sphincter 120. Light contractions near the upper stomach 720 function to start propelling the ingested materials towards the Antrum 140 of the stomach 180. Due to gravity, the fluids that are ingested will reach the Antrum 140 more quickly. Any simple sugars that are ingested are quickly dissolved into solution with the digestive secretions as well as the ingested fluids. The ingested matter and fluid components are propelled onto the upper surface 210 of the caloric bypass device. The contact of the fluid matter with the porous 235 surfaces of the caloric bypass device 200, coupled with the increased pressure from the peristaltic wave, forces the fluid through the pores or valves of the inner wall component 330 and into the free volume of the device. As the contractile wave of the stomach 180 continues and increases in the Antrum 140, the caloric bypass device 200 is subjected to increasing radial force from contact with the surface of the stomach 180. The increase of stomach contractile force is transmitted radially inwards through the wall of the mating receiver 395 and onto the standing rib-like elements 340 of the inner wall component 330. As the contractile force increases, the standing rib-like elements 340 reach a critical stress and buckle. This buckling of the standing rib-like elements 340 results in the reduction of free volume of the vertical channels 475 within the assembled caloric bypass device 200. The fluid that was previously transmitted into the free volume of the vertical channels 475 increases in pressure. In the case of the inner wall component 330 having non-reversing valve elements, the fluid pressure exerts an opening force on the anti-reflux valve 485 located at the exit of the lower end of the device 220 and is transported into the extension tube 290. In the case of the porous type of inner wall component 330, the fluid pressure required to pass through the pores of the porous 235 device is greater than the pressure necessary to open the anti-reflux valve 385 and the fluid escapes the reduced free volume space of the caloric bypass device 200 into the extension tube 290. Once the fluid has reached the extension tube 290, it is slowly transported towards the ileum, 730 and out of the extension tube exit 295. This high calorie/carbohydrate solution is thereby prevented from entering the Duodenum 170. Additionally, a small amount of the digested chyme is passed through the integral valve component of the inner wall component 330. This chyme is subjected to further granulation within the Pylorus 150 and is subsequently passed into the Duodenum 170 for further digestion and preparation for absorption of the beneficial nutrients.

Once the contractile wave has passed through the caloric bypass device 200, the relaxation of the stomach contractions enables the caloric bypass device 200 to resume the expanded state. The relief of contractile force enables the standing rib like elements 340 on the inner wall element to spring back in unison with the movement of the stomach wall and thereby reform the free volume within the caloric bypass device 200. Since the free volume is being created through the elastic expansion of the caloric bypass device 200, there is a slight negative pressure created within the free volume space. This low pressure effect facilitates the extraction of more fluid from the chyme in preparation for the next contractile wave.

Referring to FIGS. 8A through 8E, an embodiment 800 is disclosed that functions to extract the high calorie fluids from the ingested food as well as the partially digested food. The device 810 is produced with an upper region 820 that is compliant with the wall of the stomach 180. In the disclosed embodiment, the device 810 is similar to a thin walled balloon with an inflatable expansion element 1320 within. While an inflatable spiral element 1320 is illustrated in the preferred embodiment, alternate forms of expansion elements such as elastic spring like elements, or varying wall thickness to form reinforcement ribs, pleated double wall inflation channels, etc. are also feasible. While the device 810 is compliant with the wall of the stomach 180, the surface of the device 810 may be produced with small channels 860 that extend generally axially along the device. In the case where the expanded device 810 is fully compliant with the surrounding wall of the stomach 180, the channels 860 provide a passage for ingested food and chyme to pass along the porous outer surface 880 of the device 810. Alternatively, the expansive force of the compliant device 810 may be low and as such, the surface of the device may deflect away from the lining of the stomach to enable food passage between the surface of the device 810 and the lining of the stomach 180. In either version, the ingested food or liquid component of the chyme is essentially pressed against the porous outer surface of the device 810 in order to pass toward the Antrum and Pylorus. The contractile waves essentially force the ingested materials against the porous outer surface of the device which provides some level of sieving action. It should also be noted that the device may utilize valves on the surface of the device as previously disclosed, or a combination of porous material as well as the inclusion of valve elements. As the device is hollow, the pressurized fluid component is separated from the ingested materials and passes into the inner volume of the device. Once the fluid component has passed through the surface of the device, gravity causes the fluid that is contained within the device to travel towards the exit of the device where it is expelled from the lower portion 850 of the device through the anti-reflux valve 840 and into the extension tube. Ultimately the fluid traveling through the extension tube is deposited into the ileum or to locations further downstream in the gastrointestinal tract.

This particular embodiment of device 810 includes a narrow region 830 where the device is not in contact with the stomach 180. The inclusion of the narrow region enables the ingested food particles to become mixed and granulated within the Antrum 140 and a portion of Pylorous 150. The lower portion of the portion 850 is in compliance with the wall of the pyloric region of the stomach 150 which enables the further extraction of fluids prior to the passage of chyme through the pyloric valve 160 and into the Duodenum 170.

Figure 8A:
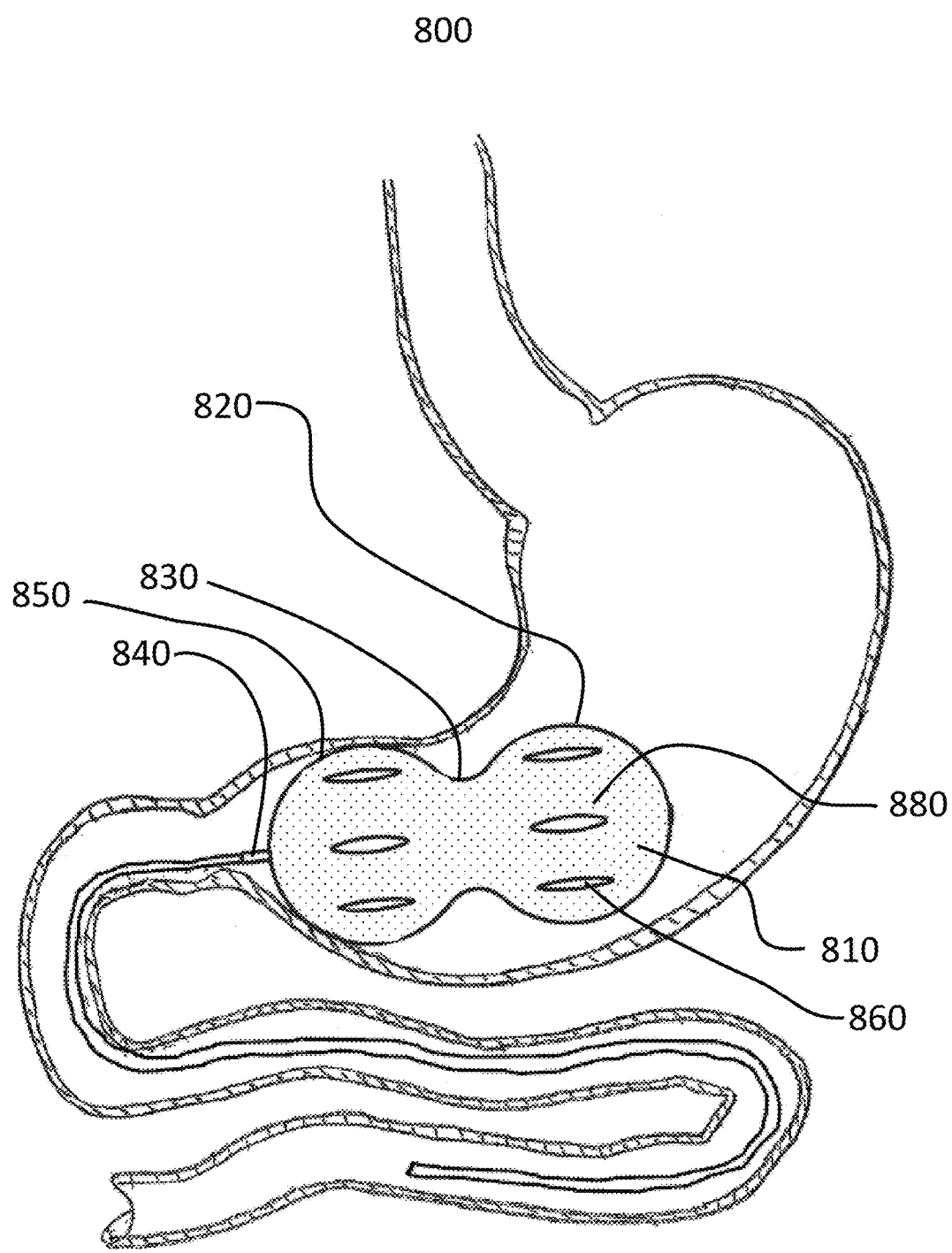
FIG. 8A illustrates an embodiment of a device of the present invention implanted in the stomach that functions to extract the high calorie fluids from the ingested food as well as the partially digested food.
Figure 8B:
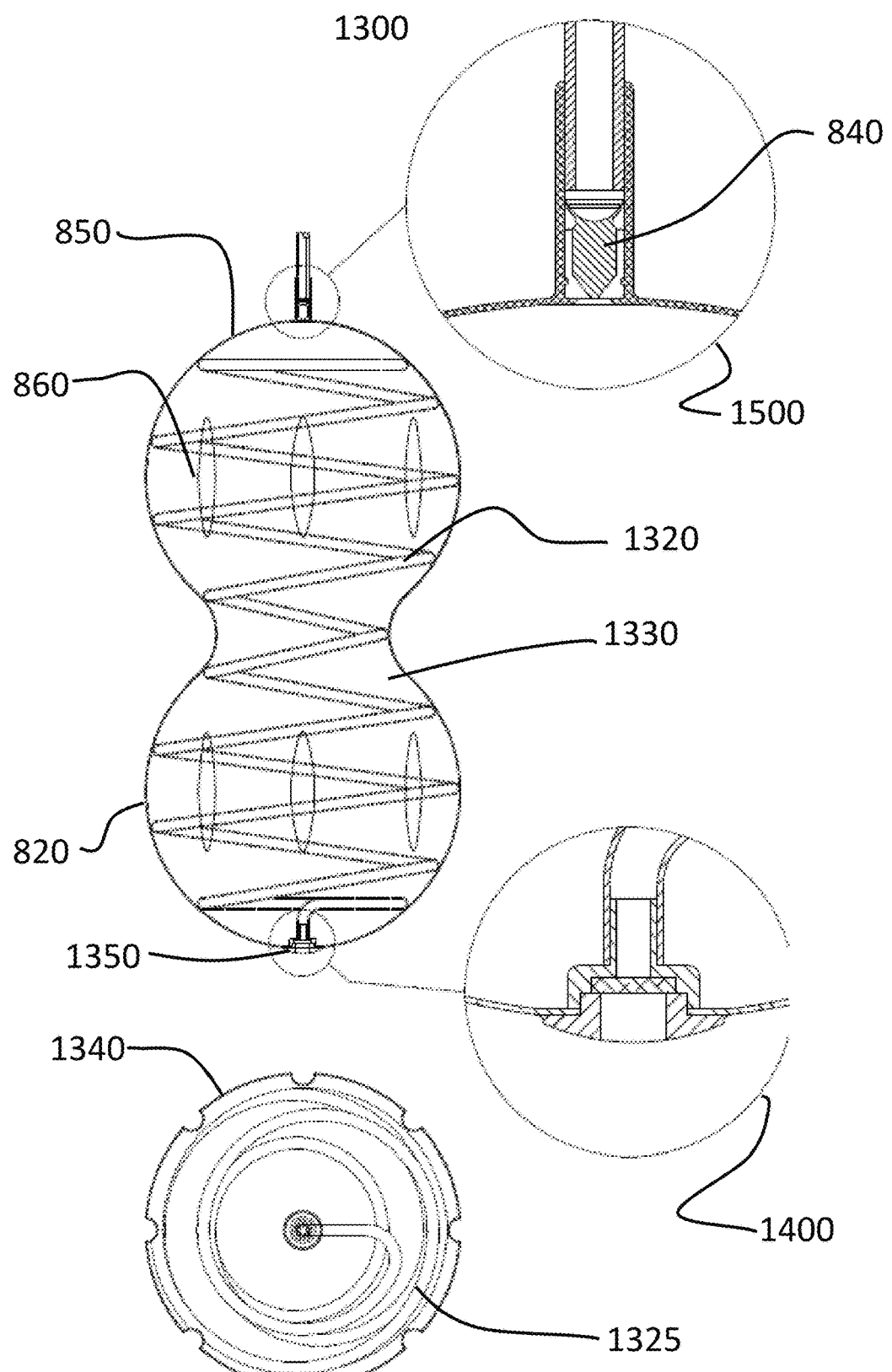
FIG. 8B illustrates the device of FIG. 8A in plan view and an end view.

The design of the device 810 is further illustrated in FIGS. 8B, 8C, 8D and 8E. Referring initially to FIG. 8B, the device 810 is illustrated in a plan view 1330 and in an end view 1340. The inflatable expansion element is attached internally to the fill port 1350 at the upper end 820 of the device 810. Further, an expanded view of the fill port is provided as FIG. 8C. On the lower portion 850 of the device 810, the anti-reflux valve 840 is also illustrated in an expanded view 1500 and will be discussed.

Figure 8C:
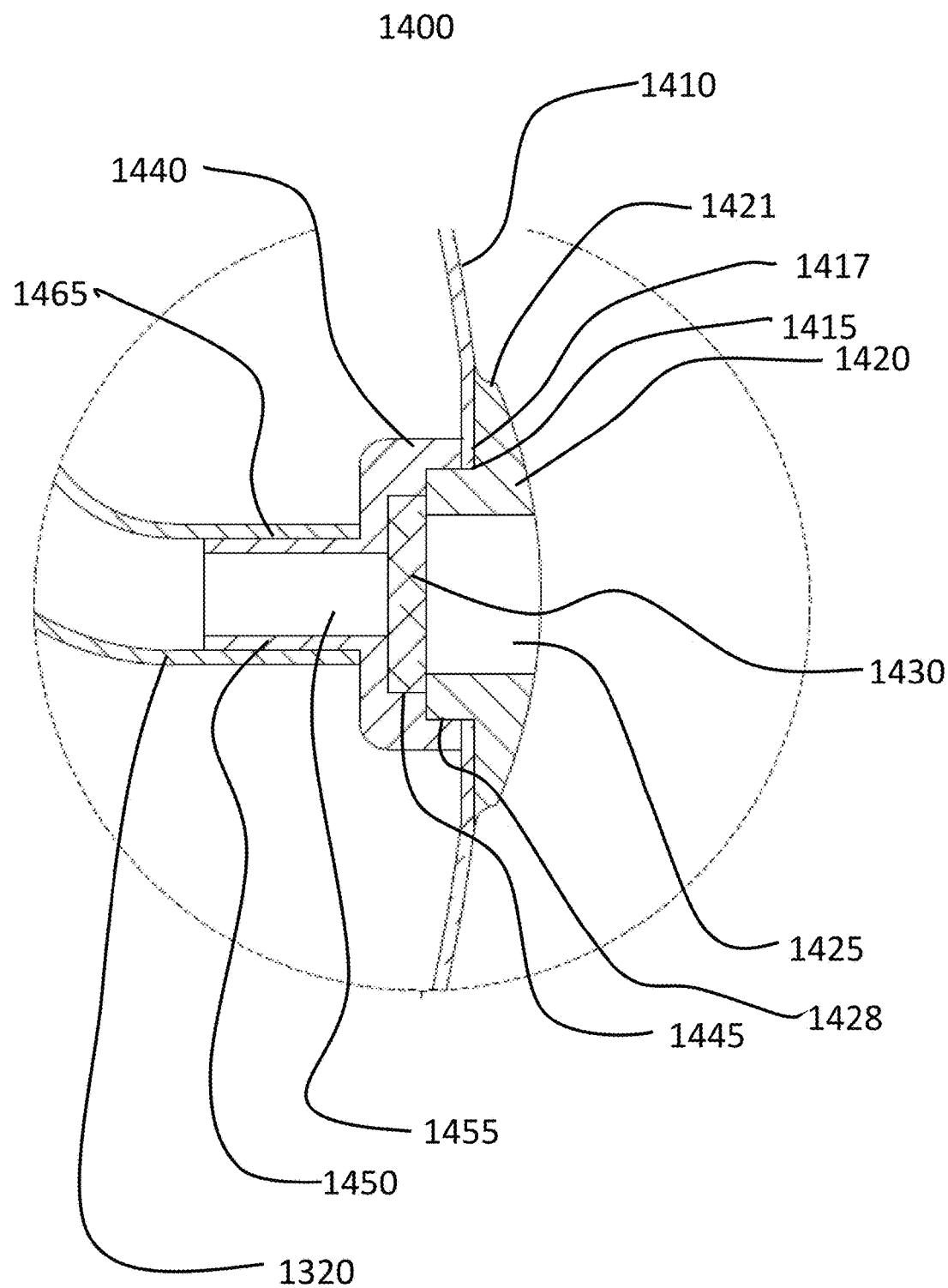
FIG. 8C is an expanded cross-sectional view of the fill port of the device of FIG. 8A.

Referring to FIG. 8C, a cross sectional view of the upper region 820 of the device 810 is illustrated. The proximal wall 1410 of the device 810 is produced with a passage 1415 that is circular in shape and is in fluid communication with the space contained within the device 810 and the space external to the device. A fill port 1420 is installed in the passage 1415. The fill port has a flange element 1421 that is in abutment with the proximal wall element 1410 as well as a through passage 1425. The fill port has a second region that is produced with a barrel feature 1428 with an external diameter that is smaller than the diameter of the flange element 1421. The barrel feature 1428 is sized to fit within the passage 1415 in the proximal wall 1410 of the device 810. A mating receiver well 1440 is mounted to the barrel feature 1428 of the fill port 1420. The two components are bonded together and to the abutting proximal wall 1410 portion that is compressed between the receiver well 1440 and the fill port 1420. A septum 1430 is located within the bore of the receiver well 1440. The septum is produced from an elastic material, such as silicone, that serves to prevent fluid communication between the inner space 1455 within the receiver well 1440 and the outer space within the through passage 1425. The septum is intended to be pierced by a needle during filling of the inflatable expansion element 1320. The receiver well 1440 is produced with a cylindrical extension tube 1450 that fits within and is bonded to the proximal end of the inflatable expansion element 1320. The cylindrical extension tube 1450 may be bonded at the interface 1465 with the inflatable expansion element through the use of adhesives, chemical, thermal or mechanical means.

Figure 8D:
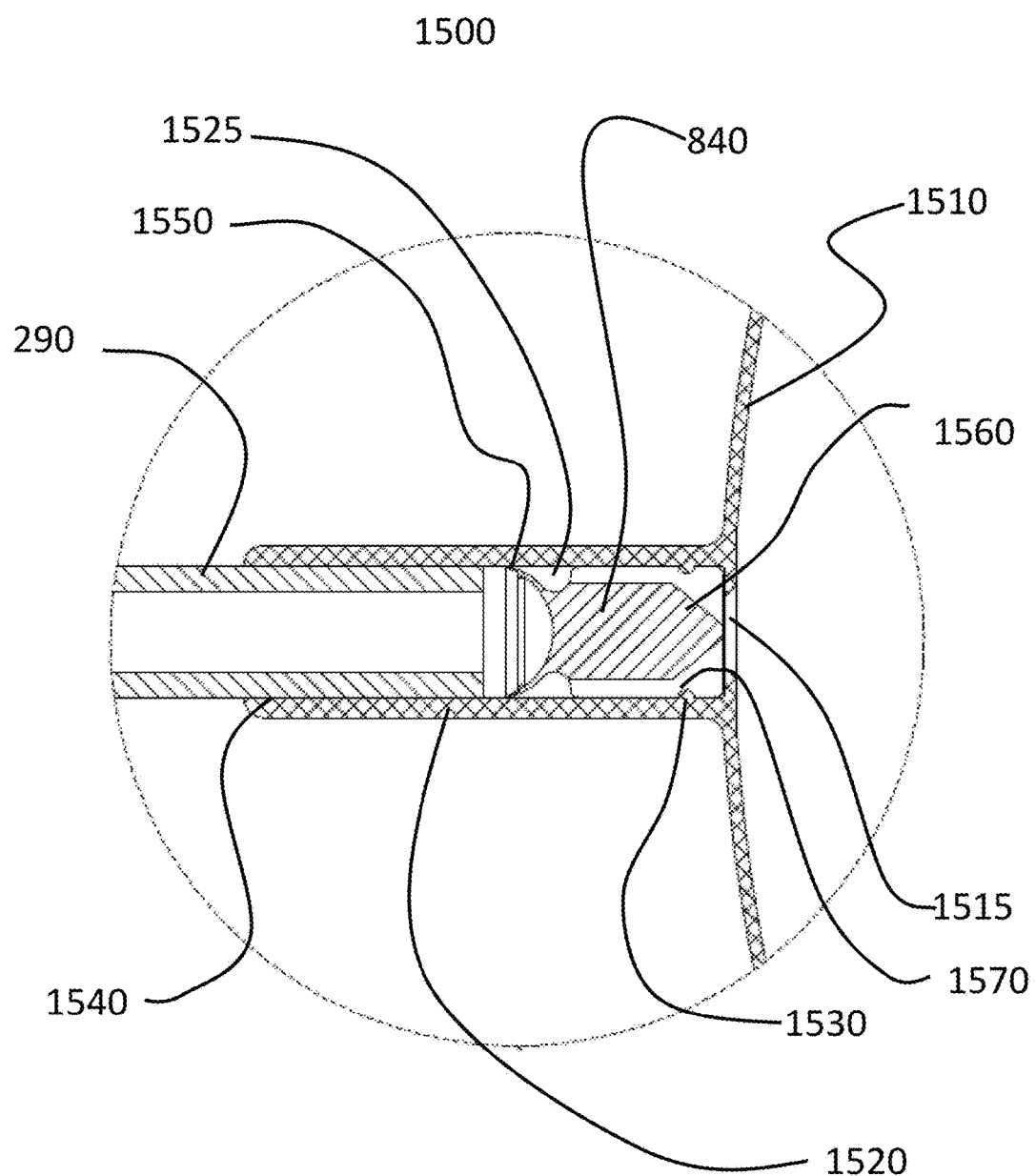
FIG. 8D is a cross-sectional view of the anti-reflux valve, the extension tube, the receiver port, and the distal wall of the device of FIG. 8A

Referring to FIG. 8D, a cross sectional assembly view 1500 of the anti-reflux valve, the extension tube 290, the receiver port 1520 and the distal wall 1510 of the device 810 are illustrated. The distal wall 1510 of the device 810 is produced with a distal passage 1515 that is in fluid communication with the inner space 1525 of the receiver port 1520. The distal end of the device 810 is produced with a cylindrical receiver port 1520. The inner surface of the cylindrical receiver port may be produced with a protruding feature 1530 such as a ring like rib that extends about the inner diameter of the receiver port 1520. The protruding feature 1530 engages with a mating receiver feature 1570 that is located on the anti-reflux valve 840. The anti-reflux valve 840 is pressed into the receiver port 1520 until it is seated against the distal wall of the device 810 until it engages with the protruding feature 1530. Once the anti-reflux valve 840 is seated in the proper position, the proximal end of the extension tube 290 is inserted into the open end of the receiver port 1520 to a depth that does not interfere with the distal end 1550 of the anti-reflux valve 840. The extension tube 290 is bonded into the receiver port 1520 at the interface 1540. The bonding of the two components together may be done through the use of adhesives, chemical or energy based bonding methods, as well as mechanical attachment.

Figure 8E:
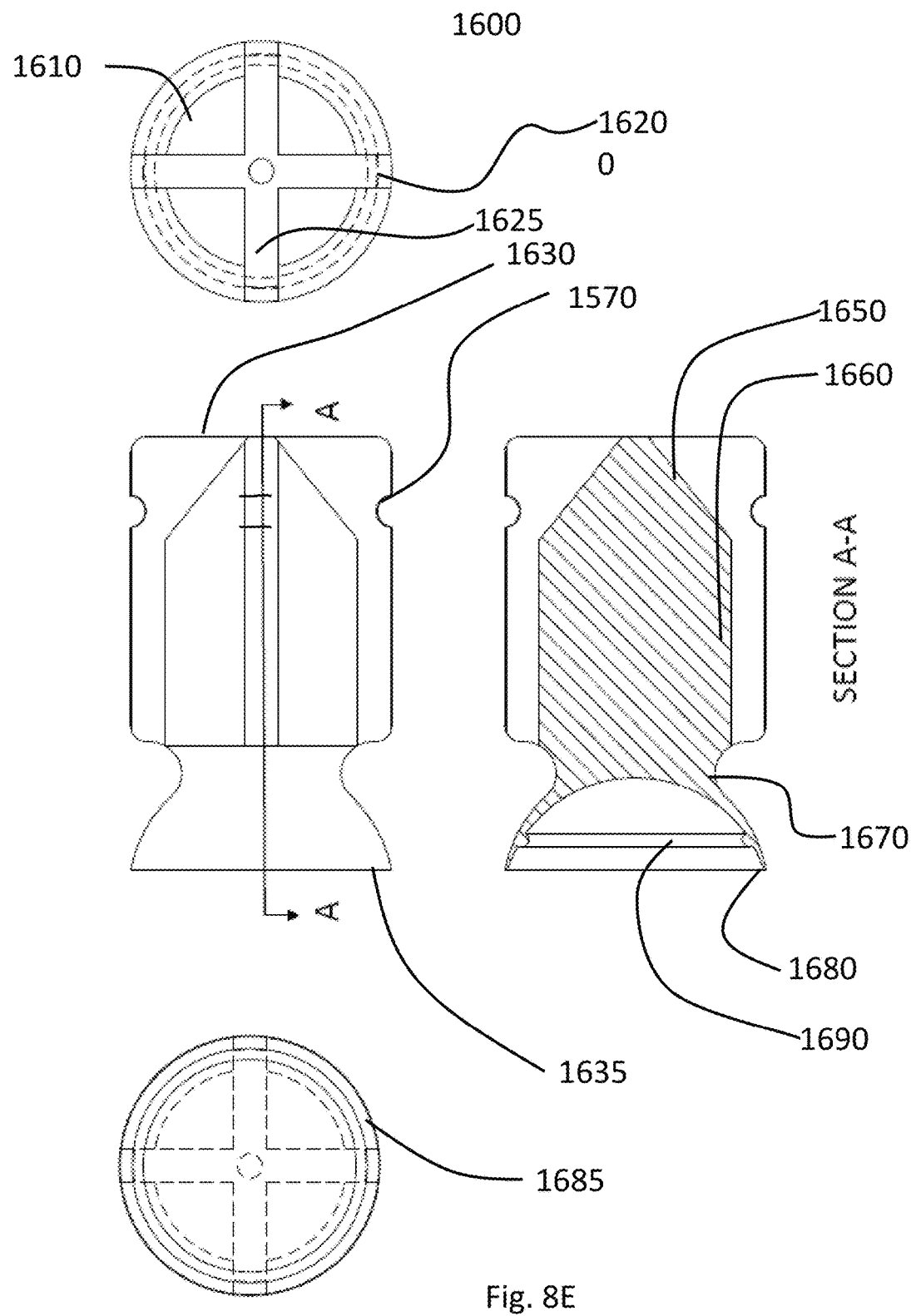
FIG. 8E is a plan view of the anti-reflux valve of FIG. 8D showing the side, the two ends and a cross-section.

Referring to FIG. 8E, the anti-reflux valve 840 is illustrated. A plan view 1600 showing the side and the two ends as well as a cross sectional view is shown. The anti-reflux valve 840 may be made of an elastomeric material such as silicone, rubber, or other flexible materials such as polyurethane or other thermoplastic elastomers. The form of the anti-reflux valve 840 is generally cylindrical with a varying cross sectional area. The proximal end 1630 of the anti-reflux valve is formed into a somewhat cruciform cross sectional shape with two ribs 1620 and 1625 extending from a central location about the long axis of the part. The face of each of the ribs 1620 and 1625 are produced with a recessed feature 1570. The use of the intersecting ribs 1620 and 1625 results in a series of parallel channels 1610 that extend axially away from the proximal end 1630 of the anti-reflux valve 840. When assembled into the cylindrical receiver port 1520, the presence of the channels 1610 enable fluid communication from the distal passage 1515 in the inner space 1525 through the channels 1610 and into the small diameter skirt base 1670. Extending distally from the skirt base 1670, is the skirt 1685 which terminates at a fine wall thickness edge 1680. Since the cross sectional area of the skirt 1685 becomes very thin near the terminal edge 1680, an optional reinforcement ring 1690 may be included. The reinforcement ring 1690 may be formed as an integral feature within the skirt 1685 or it may be added as a separate component. The resultant skirt has a slightly self-supporting geometry; however, it is highly susceptible to collapsing inward about the central axis of the part. In this manner, when installed inside of the receiver port 1520, the skirt 1685 may collapse away from the inner wall of the receiver port 1520 when fluid travels though the distal passage 1515 from within the device 810 through the inner space 1525 and past the exterior surface of the skirt 1685 and into the extension tube 290. When the peristaltic wave compresses the chyme within the distal portion of the extension tube 290, the fluid contained within the extension tube 290 potentially could be propelled proximally through the extension tube 290 and into the receiver port 1520 and into the central portion of the skirt 1685. The fluid pressure builds against the inner surface of the skirt 1685 and causes the terminal edge 1680 to flare out against the inner surface of the receiver port 1520 thereby forming a seal against the regurgitation of the fluid into the device 810 during the distal peristaltic contraction.

Figure 9:
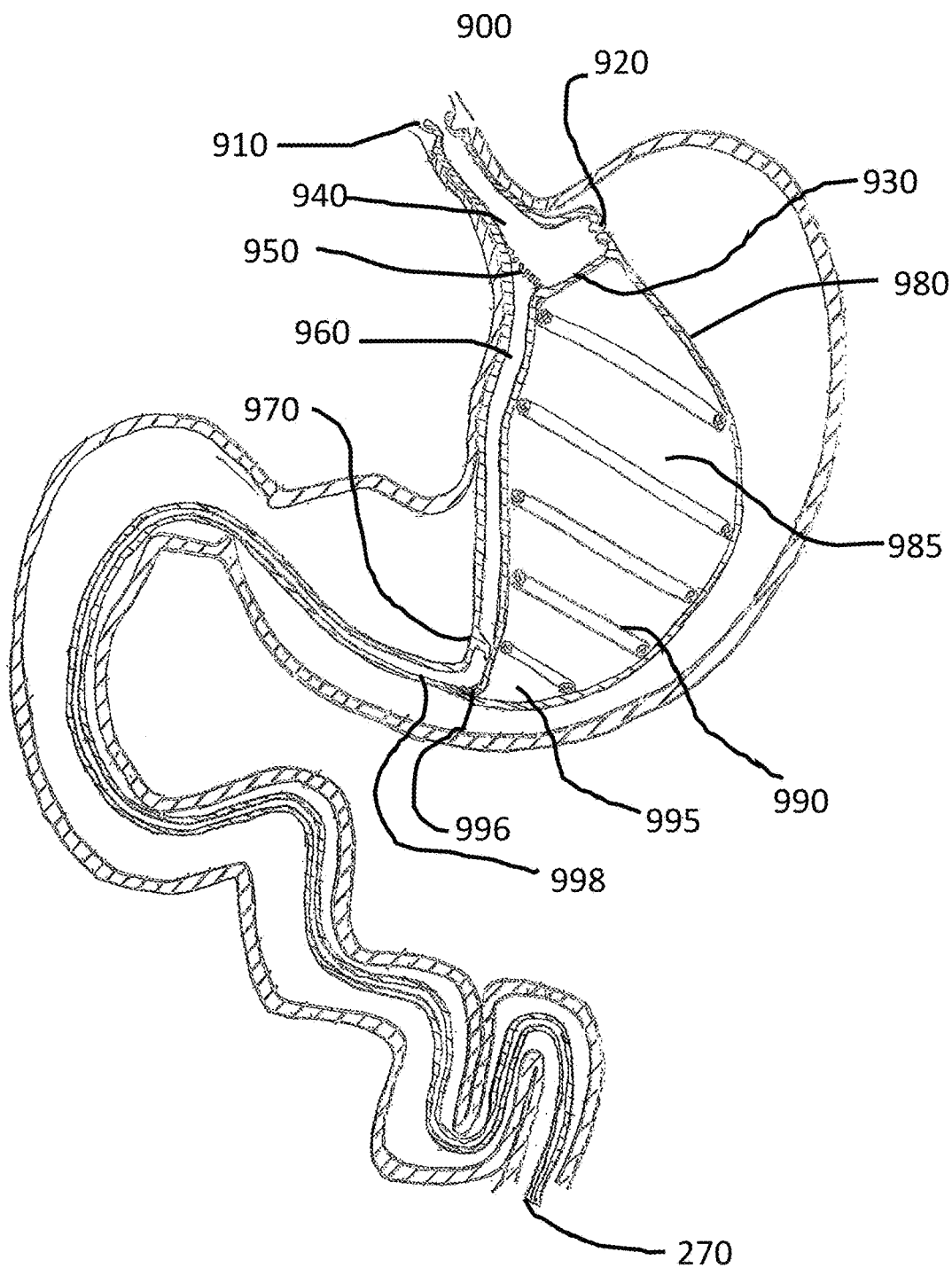
FIG. 9 illustrates a deployed embodiment of a device of the present invention that provides for solid-liquid separation.

Referring to FIG. 9, a cross-sectional view of a deployed flat film based device 900 is disclosed whereby the flat film based device 900 provides a first stage separation of the fluid component from the ingested materials as the materials are passed from the lower esophageal sphincter 120. The flat film based device 900 is produced as a hollow structure and may be produced from the welding of two layers of thin film along the perimeter and at the boundary locations. The upper portion 910 of the device is engaged with the lower esophageal sphincter 120. The engagement of the upper portion may be achieved through the use of integrated barbed elements, integral stent like components or direct fixation with staples, sutures or tacks or other such means of mechanical bonding to local tissues. In this position, the ingested food particles and fluids will be forced into the interior volume 940 of the upper portion 910 of the device 900. The food passes over a macro-porous element 950. As the ingested materials pass over the macro-porous element 950, any fluid that is ingested passes into the upper portion of the bypass channel 960. In order to maximize the opportunity for solid liquid separation to occur within the upper portion 910, there is a valve element 920 that inhibits the exit of the ingested food particles from within the interior volume region 940 of the device. Once there is sufficient volume of ingested material within the interior volume of the device, it passes through the valve and into the Fundus 130 of the stomach 180 for exposure to the secreted digestive enzymes. The valve element 920 may be a simple slit type valve with a thickened ring of material which is capable of expanding and opening when pressurized from within, alternatively, the valve element may be replaced by a simple flow restriction element such as a narrowed orifice. In either case, the ingested particles are delayed from immediate emptying into the stomach 180 to provide the extra time necessary to allow the separation of the fluid into the upper portion of the bypass channel 960. Fluidic materials that are collected within the bypass channel 960 will travel towards the lower portion of the channel where it is passed through a bypass anti-reflux valve 970.

The device is also comprised of a third compartment 980 that has an inner volume 985 that is produced with an elastic expansion element 990 within. The compartment 990 may be produced with a directionally favorable passage that crosses from the exterior volume into the third compartment 980 of the device 900. Valves, pores or other means are provided to enable the passage of fluid and very fine particles through the flat film based device 900. The chyme is in contact with the outer surface of the flat film based device 900. Contractile waves of the stomach 180 cause the compression of the chyme against the outer surface of the flat film based device 900. The enclosed elastic expansion element 990 resists the pressure of the chyme on the flat film based device 900. The compression of the chyme against the surface of the flat film based device 900 causes fluid to enter the inner volume 985 while also causing the elastic expansion element 990 to partially collapse as well thereby reducing the inner volume of the compartment 985. Relaxation of the contractions allows the slightly compressed compartment 980 to expand due to the re-expansion of the elastic element 990 contained within the third compartment. The expansion of the elastic expansion element 990 expands the inner volume 985 of the third compartment 980 which creates a small low pressure zone within the inner volume 985 of the third compartment 980. The low pressure within the inner volume 985 causes a negative relative pressure gradient across the porous flat film device 900 enabling the passage of fluidic materials into the inner volume 985 of the flat film based device 900. Due to gravity, any fluid collected within the inner volume 985 travels to the lower end 995 of the flat film based device 900 in the proximity of the exit anti-reflux valve 996. Subsequent contractions of the stomach 180 cause the fluid to be passed from within the inner volume 985 into the common bypass tube 998. The fluids from the upper portion of the bypass channel 960 and the inner volume 985 are subsequently transported through the common bypass tube 998 and to the exit 270 located within or past the ileum.

Figure 10:
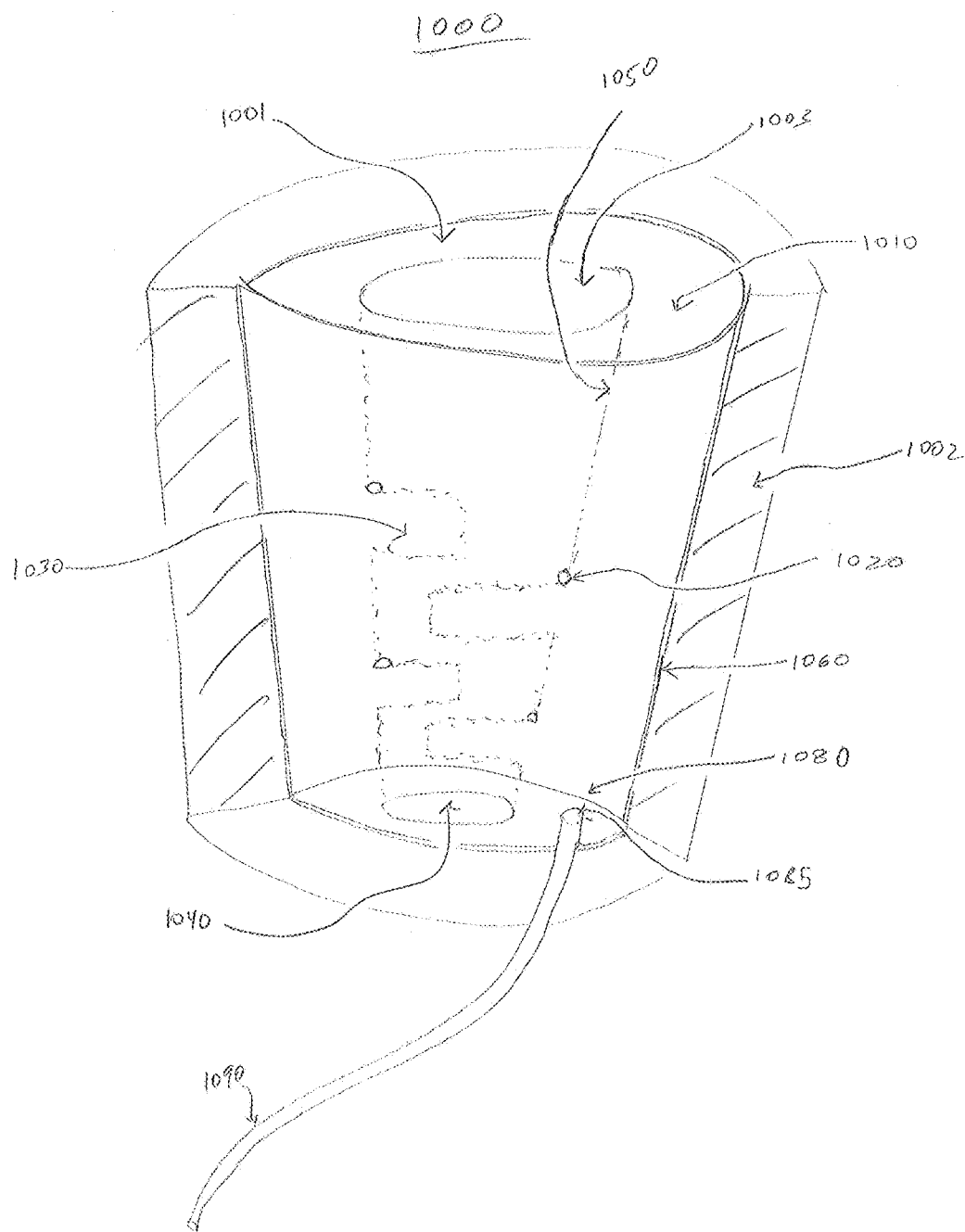
FIGS. 10 and 11 illustrate a side view and a top view of another embodiment of the present invention wherein the inner wall component contains baffles.
Figure 11:
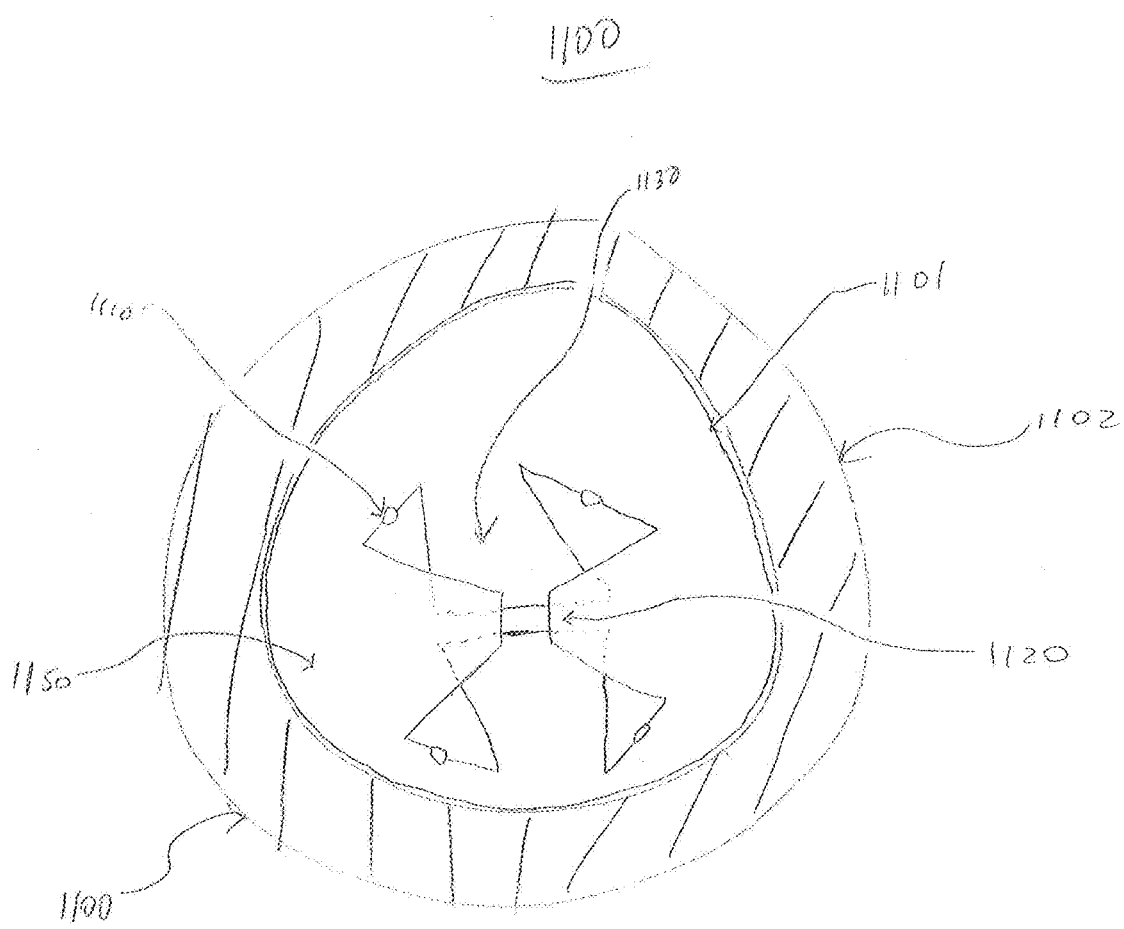

FIGS. 10 and 11 illustrate another embodiment of the present invention wherein the device 1000 has an inner wall component 1001, with an opening 1003 to allow chyme and digested material to enter into and an exit 1040 to allow digested food to exit, and an outer receiver component 1002. The inner wall component 1001 contains baffles 1030 on the inner luminal surface 1050 where chyme moves through. This inner wall component 1001 is compliant and may be made from materials such as silicone, polyethylethenes such as polyethylene terephthalate, polyurethane, fluoropolymers such as polytetrafluoroethylene (PTFE), polypropylene, polyvinyl alcohol or other biocompatible polymers. The material used is preferably resistant to prolonged exposure to acidic environments found in the stomach. In one embodiment, more than one material can be used to fabricate the device. In one embodiment, the outer receiver component 1002 is made from a different material than the inner wall component 1001. The inner wall component 1001 is hollow and has an inner surface 1050 and outer surface 1060, with the inner surface 1050 having the baffles 1030 as well as openings 1020 in the wall 1010 that allow movement of fluid from the inner surface 1050 of the device to the hollow chamber 1080 within the wall 1010. The entire inner wall component 1001 can be inserted into the outer receiver component 1002 in a similar fashion to that illustrated in FIG. 4. The fluid entering the hollow chamber 1080 collects at the bottom of the hollow chamber 1080 and exits through a larger opening 1085. This fluid can then be transported into the exit tube 1090. FIG. 11 illustrates a top-down view of the device 1100 having an inner wall component 1101 and an outer receiving component 1102. Opposing baffles 1120 and 1130 are staggered vertically so that the flow of chyme is churned. This enables better separation of the fluid component of chyme from the solid particles that are only partially digested. The fluid is then able to enter at least one of the openings 1110 and subsequently flow into the hollow component 1150 of the inner wall component 1101.

Figure 12:
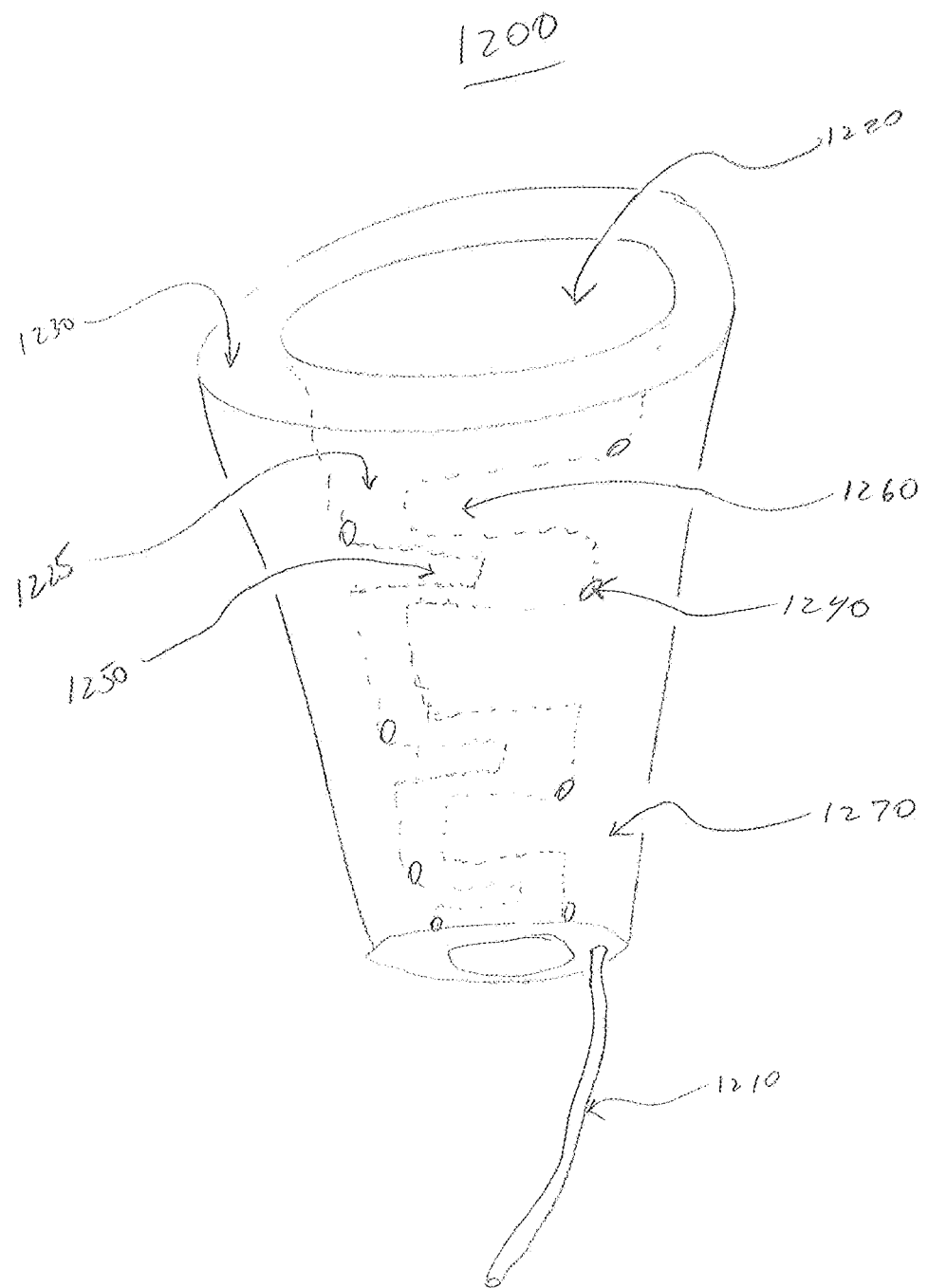
FIG. 12 illustrates another embodiment of the present invention wherein the device is a single unit having an internal lumen with baffles.
Figure 13:
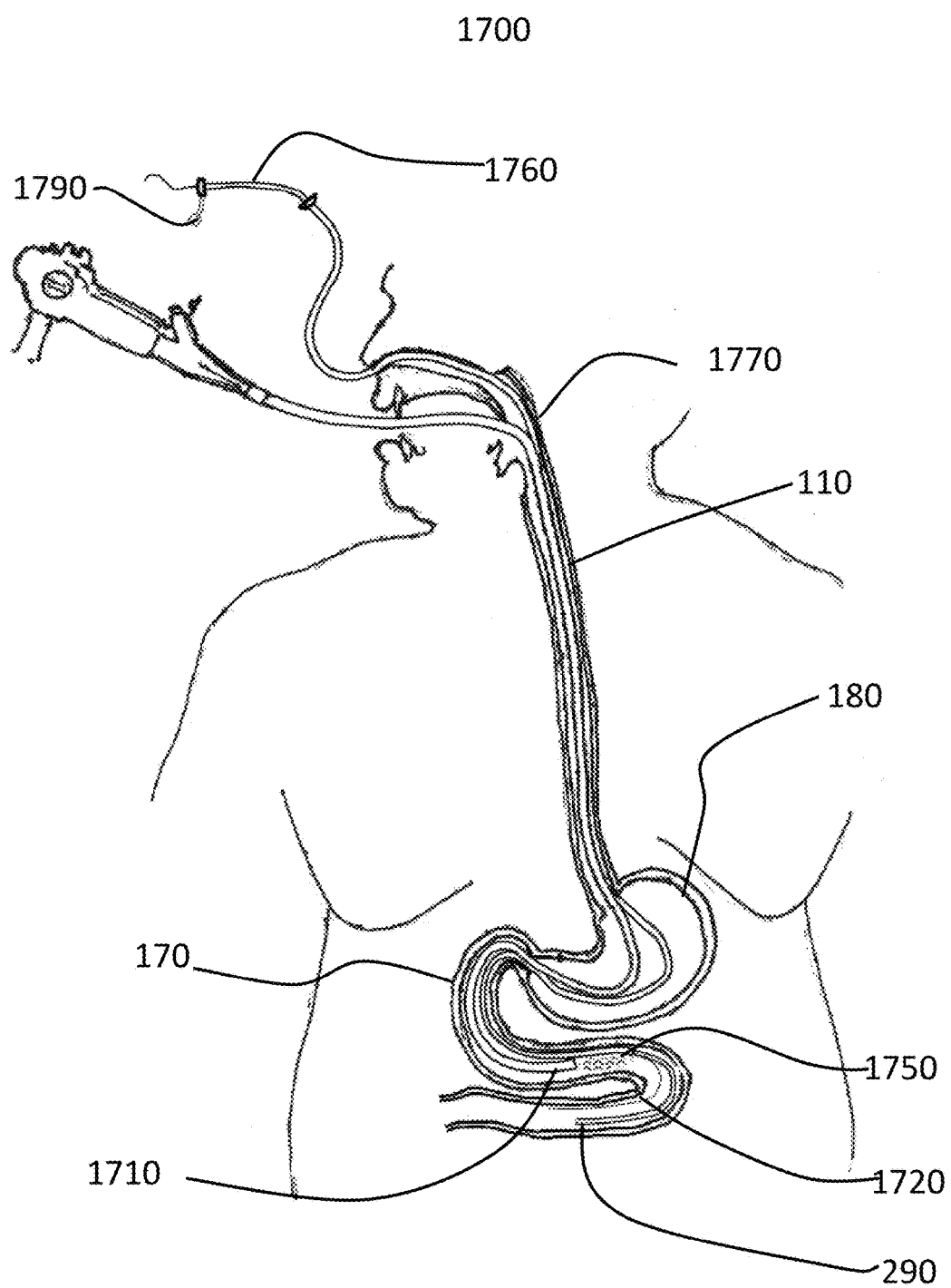
FIGS. 13-17 illustrate a procedure for the deployment of the caloric bypass devices of the present invention in a patient's stomach.
Figure 14:
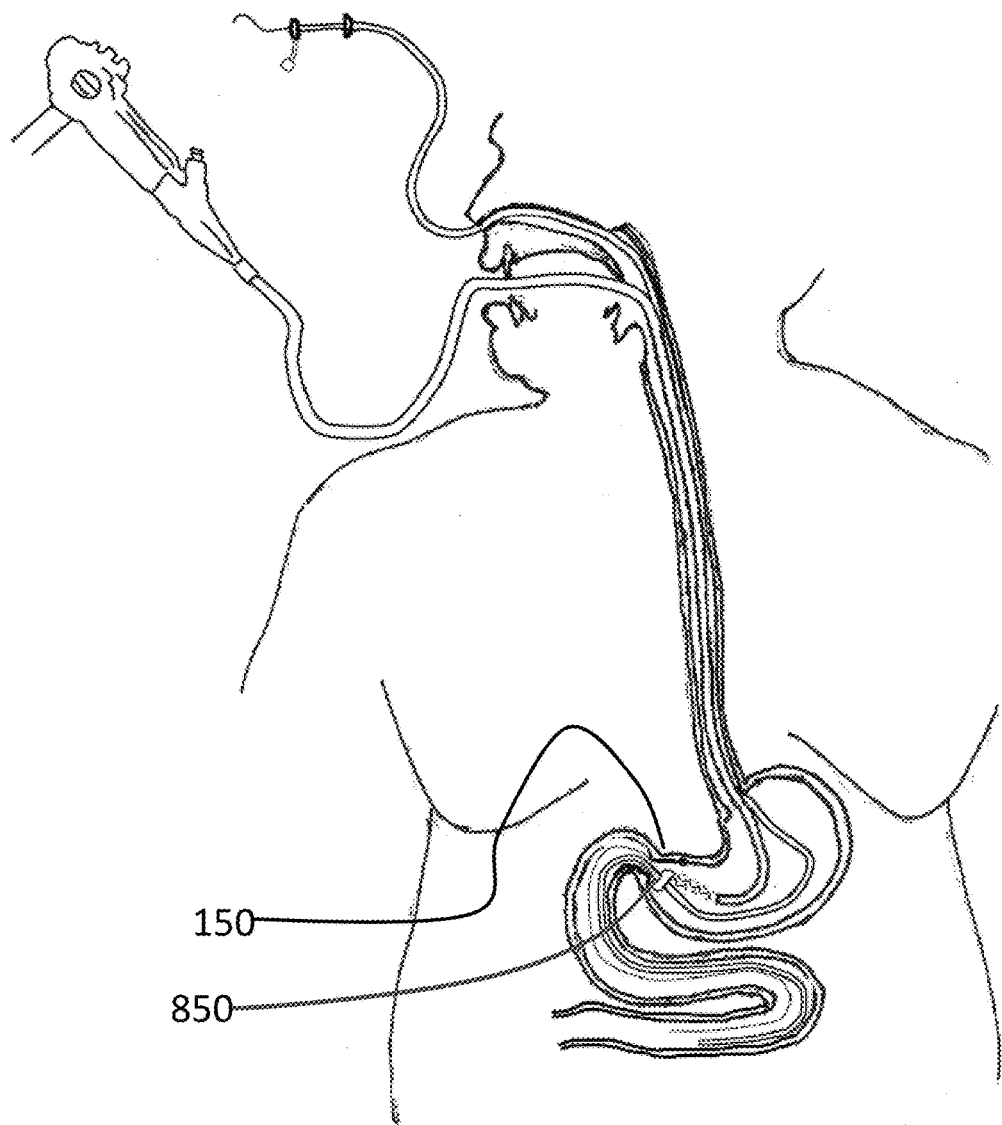
Figure 15:
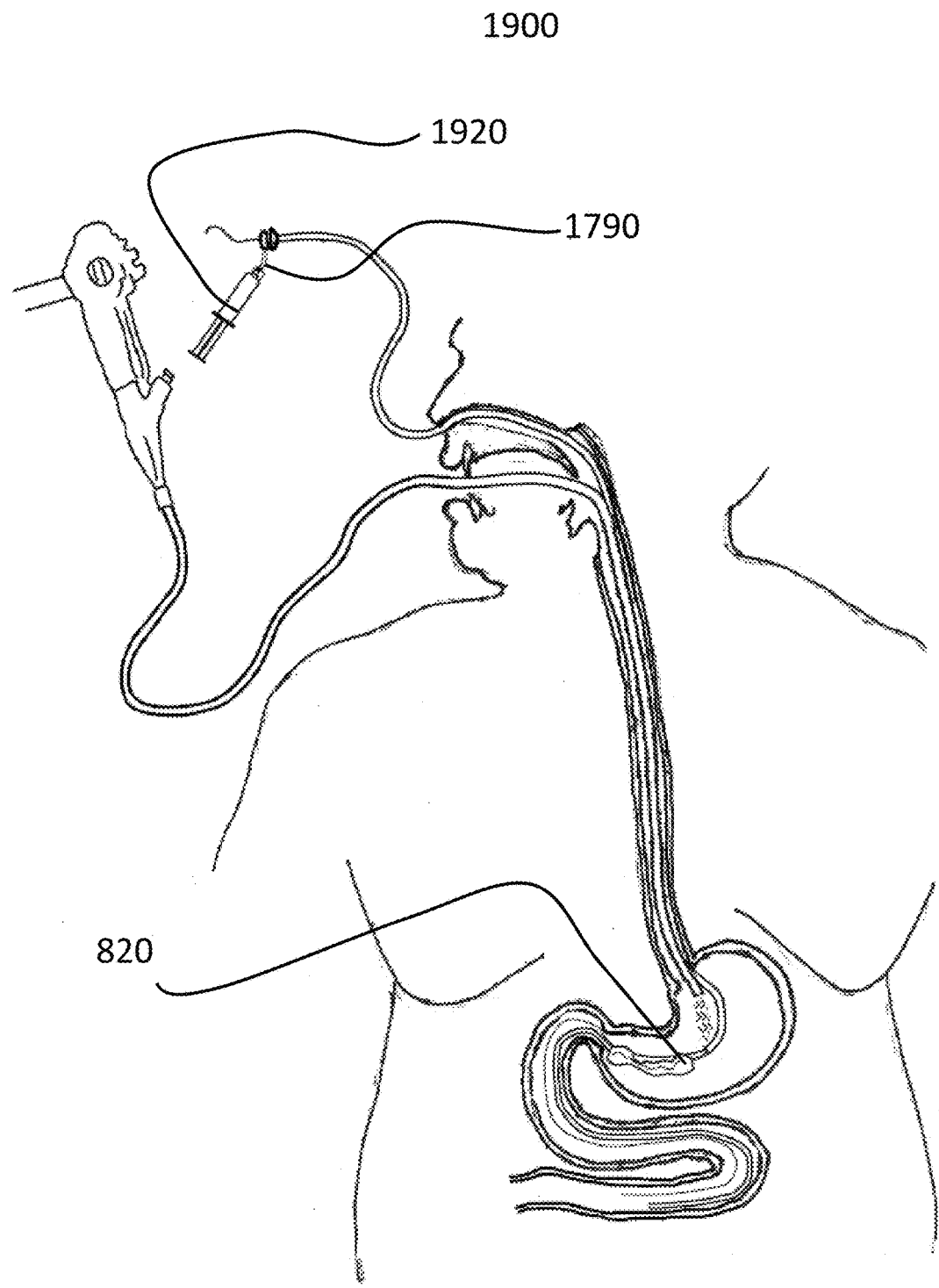
Figure 16:
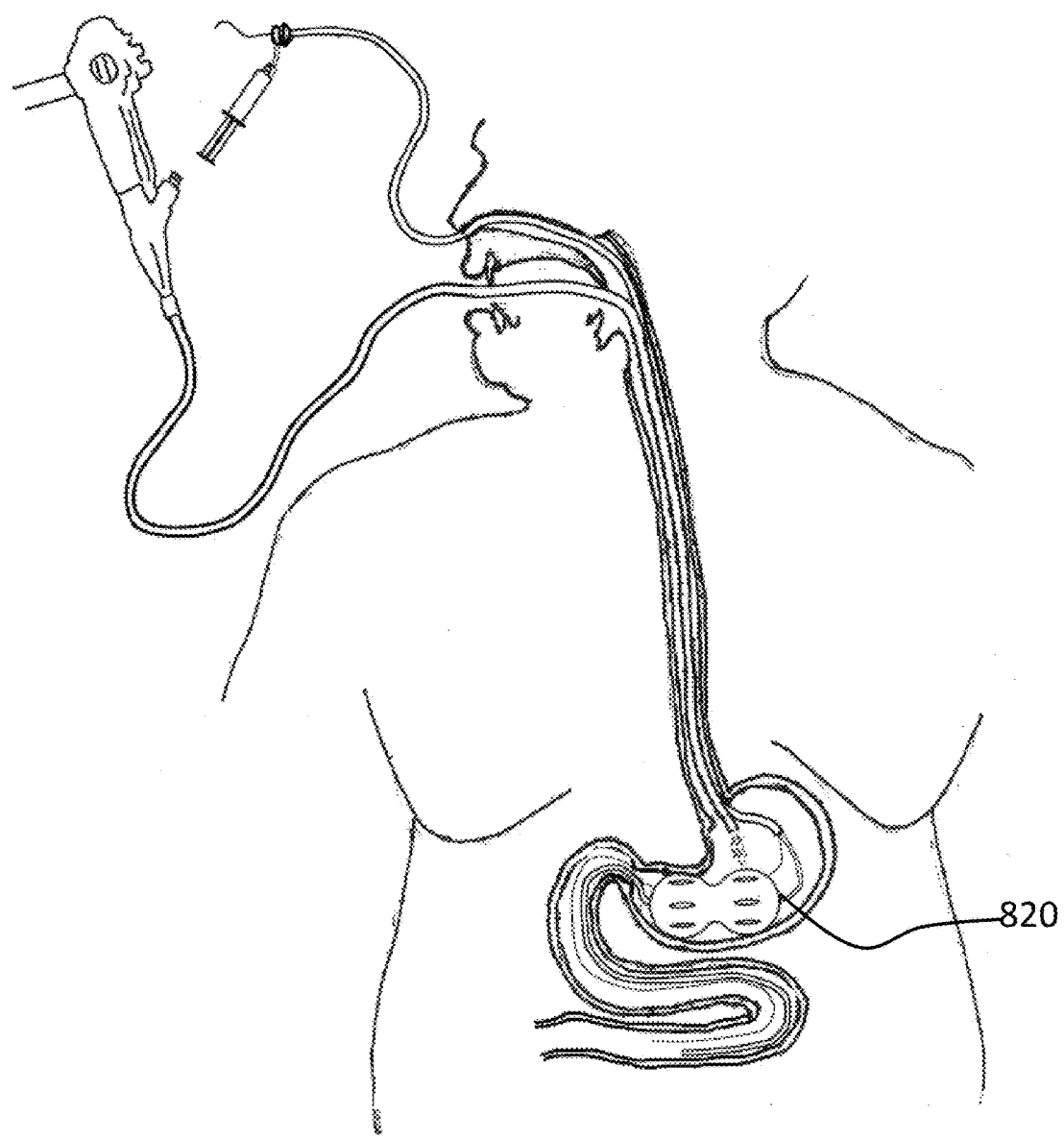
Figure 17:
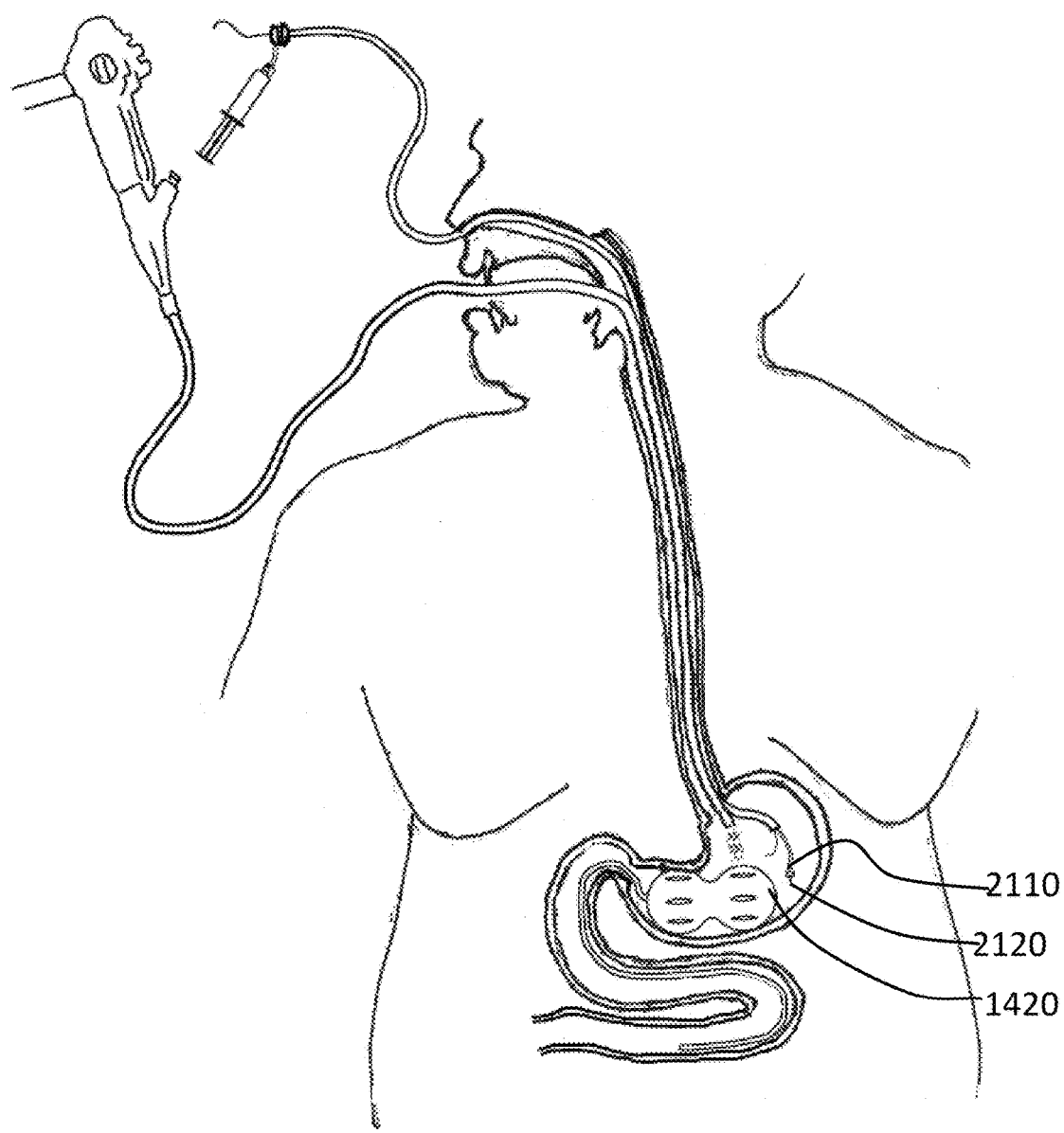

FIG. 12 illustrates yet another embodiment of the device. In this embodiment, the device 1200 is a single unit having a wall 1230 and a proximal opening 1220 for chyme to enter. The entire device 1200 is compliant and preferably made from a biocompatible polymer such as silicone. The inner lumen 1225 of the device has baffles 1250 and 1260 that are opposed and overlapping. This arrangement of baffles 1250 and 1260 enables churning of chyme and increased separation of fluid from more sold chyme. The fluid can then enter the hollow chamber via openings 1240 and flow into the hollow chamber 1270 where it can collect by gravity or other passive means near the tube 1210 that enables the fluid to bypass the proximal segment of the duodenum. In this embodiment, an outer receiver element is not used.

It will be appreciated that the caloric bypass devices of the present invention can have a variety of geometric configurations and surface geometries, including but not limited to conical, cylindrical, frustoconical, spherical, etc., and combinations thereof. Different sections of the devices may have different adjacent geometric configurations and surface geometries.

While various embodiments of the subject invention are disclosed, each embodiment provides the means for the extraction of fluid with solubilized sugars and dispersed starches to enter within a free space of a device and to be transported away from the primary location of absorption. Additionally, the transportation of a significant portion of the sugars and starches away from the site of absorption emulates two aspects of the Duodenal switch surgeries. One aspect is that the sugars are not absorbed and the second aspect is that the deposition of sugars directly into the ileum provide a biological feedback stimulus to the patient. This biofeedback, in the form of dumping syndrome, helps to teach the patient to avoid foods that are high in sugar and simple starches and thereby drives a behavioral change. Additionally, since the device is temporary in nature, and is delivered through an upper GI endoscopic approach, it may be retrieved as necessary or after patient behavior has been acceptably modified.

Referring to FIGS. 13-17, the caloric bypass devices of the present invention may be deployed in a patient's stomach utilizing the following insertion procedure. The patient may be seated in a reclined position or may be laid flat on a table. Sedation is administered in a conventional manner and topical anesthetic may be applied to the surface of the oropharynx 1770. A conventional, flexible steerable endoscope 1710 is passed into the esophagus 110 and is passed distally through the stomach 180 and into the duodenum to the desired location for the bypassed material to be deposited into the distal intestinal tract. A guide wire 1720 is placed through the endoscope 1710 and the endoscope 1710 is withdrawn. A catheter 1750 with the compacted device 810 inside as well as the flexible fill tube 1790 is passed over the guide wire 1720. The endoscope 1710 is passed alongside the catheter 1750 thereby enabling visualization of the advancement of the delivery catheter 1750. Upon reaching the target location for the delivery of the distal portion of the device 810 and more particularly the distal end of the extension tube 290, the outer sheath of the delivery catheter 1750 is partially withdrawn while the pusher tube 1760 is held fixedly in place to release the compacted extension tube 290. The endoscope 1710 and the outer sheath of the delivery catheter are withdrawn further which ultimately reveals the lower portion 850 of the device 810 slightly within the pylorus 150. Once the placement of the lower portion 850 of the device 820 is confirmed to be at the proper location, the outer sheath of the delivery catheter 1750 is fully retracted over the pusher tube 1760 to fully release the device 810 within the stomach 180 of the patient which reveals the upper region 820 of the device 810. A pressure source, such as a syringe 1920, filled with sterile water, or if preferred, a filtered gas supply, is connected to the fill tube 1790. Fluid or gas is added to the device through the fill tube 1790 until the device is fully expanded within the stomach. It should be noted that the filler tube is connected to the inflatable expansion element 1320 contained within the device 820 as previously described. The pressurization of the spiral shaped inflatable expansion element 1320 causes the device to fully expand with a volume contained within the device 820 as previously described. Once the pressure has reached the maximum desired pressure within the inflatable expansion element 1320, the filler tube distal fitting 2110 is ejected from the fill port 1420. The needle 2120 located on the end of the filler tube distal fitting 2110 is produced with a barb feature on the outer surface that is engaged with the septum 1430. As the pressure within the inflatable expansion element increases, the septum 1430 expands proximally within the fill port 1420 and releases the barbed element of the needle 2120 thereby disconnecting the fill tube 2110 from the device 810. The attending physician will note that the device is been fully filled as the pressure experienced during the filling stage will rapidly decline. Once this pressure drop is detected, the attending physician will remove the delivery catheter 1750, the flexible endoscope 1710 and the guide wire 1720. The patient is released for normal daily activities.

While the proposed method of delivery as outlined utilizes a guide wire approach as well as a parallel passage of a flexible endoscope, alternatively, the delivery catheter may be sized such that it may be passed directly within the working passage of the flexible endoscope and thereby eliminate the need for a guide wire.

Although this invention has been shown and described with respect to detailed embodiments thereof, it will be understood by those skilled in the art that various changes in form and detail thereof may be made without departing from the spirit and scope of the claimed invention.

We claim:

1. A caloric bypass device, comprising:
   an expandable device having a proximal end, a distal end, an upper region near the proximal end, a lower region near the distal end, and a narrow region between the upper and lower region, wherein the narrow region has a smaller outer dimension than the upper and lower regions, and wherein the expandable device has a hollow interior and a porous outer surface in fluid communication with said hollow interior; and
   an extension tube extending from the distal end and having a channel therethrough, wherein the extension tube channel is in fluid communication with the hollow interior of the expandable device.

2. The device according to claim 1, wherein the porous outer surface has a plurality of longitudinal channels therein.

3. The device according to claim 1, further comprising an anti-reflux valve positioned between the distal end of the expandable device and the extension tube, wherein said valve is configured to allow fluid within said hollow interior of said expandable device to pass through to said extension tube.

4. The device according to claim 1, wherein the lower region is sized and shaped such that at least a portion of its porous outer surface engages an interior lining of a patient's stomach.

5. The device according to claim 4, wherein the outer dimension of the narrow region is sized and shaped such that it does not engage said interior lining.

6. The device according to claim 1, further comprising an expansion member for expanding said expandable device.

7. The device according to claim 6, wherein the expansion member is an elastic spring.

8. The device according to claim 7, wherein the expansion member is a spiral element extending along at least a portion of a length of said expandable device.

\* \* \* \* \*